United States Patent [19]

Nakagawa et al.

[11] Patent Number: 4,814,328
[45] Date of Patent: Mar. 21, 1989

[54] CEPHALOSPORIN DERIVATIVES, AND ANTIBACTERIAL AGENTS

[75] Inventors: Susumu Nakagawa; Norikazu Otake; Ryosuke Ushizima, all of Okazaki, Japan

[73] Assignee: Banyu Pharmaceutical Co., Ltd., Tokyo, Japan

[21] Appl. No.: 911,780

[22] Filed: Sep. 26, 1986

[30] Foreign Application Priority Data

Mar. 19, 1986 [JP] Japan .................................. 61-59368

[51] Int. Cl.$^4$ .................. C07D 501/46; A61K 31/545
[52] U.S. Cl. ..................................... 514/205; 540/222; 540/225; 540/226
[58] Field of Search ............... 540/222, 225, 226, 227, 540/219; 514/205

[56] References Cited

U.S. PATENT DOCUMENTS

| | | | |
|---|---|---|---|
| 4,098,888 | 7/1978 | Ochiai et al. | 540/222 |
| 4,152,432 | 5/1979 | Heymes et al. | 540/227 |
| 4,160,830 | 7/1979 | Morimoto et al. | 514/202 |
| 4,168,309 | 9/1979 | Ayres | 540/222 |
| 4,200,575 | 4/1980 | Numata et al. | 540/222 |
| 4,260,747 | 4/1981 | Heymes et al. | 540/227 |
| 4,264,595 | 4/1981 | Numata et al. | 540/222 |
| 4,379,787 | 4/1983 | Lunn et al. | 540/222 |
| 4,382,931 | 5/1983 | Lunn et al. | 540/222 |
| 4,382,932 | 5/1983 | Lunn et al. | 540/222 |
| 4,396,619 | 8/1983 | Lunn et al. | 540/225 |
| 4,396,620 | 8/1983 | Lunn | 540/224 |
| 4,406,899 | 9/1983 | Aburaki et al. | 540/222 |
| 4,416,879 | 11/1983 | Takaya et al. | 540/222 |
| 4,457,929 | 7/1984 | Kamachi et al. | 544/222 |
| 4,525,473 | 6/1985 | Aburaki et al. | 514/202 |

FOREIGN PATENT DOCUMENTS

| | | |
|---|---|---|
| 111935 | 6/1984 | European Pat. Off. |
| 121244 | 10/1984 | European Pat. Off. |
| 137440 | 4/1985 | European Pat. Off. |
| 137442 | 4/1985 | European Pat. Off. |
| 1399086 | 6/1975 | United Kingdom |

OTHER PUBLICATIONS

Journal Amer. Chem. Soc., vol. 72, p. 2989.
Organic Syntheses, Coll. vol. 5, pp. 406, 1064.
Burger, "Medicinal Chem.", 2nd Ed., (1960), pp. 42–43.
Nakagawa et al., ICAAC Abstract, Sept. 1985.

*Primary Examiner*—Nicholas S. Rizzo
*Attorney, Agent, or Firm*—Oblon, Fisher, Spivak, McClelland & Maier, P.C.

[57] ABSTRACT

The compound having the formula:

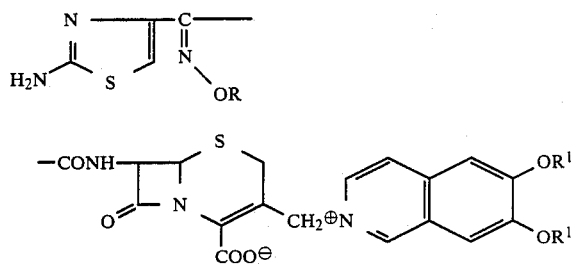

wherein R is a straight chain, branched chain or cyclic lower alkyl, a lower alkenyl or a lower alkynyl group which may be substituted by a carboxyl group, and $R^1$ is hydrogen atom or an acetyl group; or a pharmaceutically acceptable salt, physiologically hydrolyzable ester or solvate thereof.

12 Claims, No Drawings

4,814,328

CEPHALOSPORIN DERIVATIVES, AND ANTIBACTERIAL AGENTS

BACKGROUND OF THE INVENTION

1. Field of the Invention

The present invention relates to novel cephalosporin derivatives, processes for their preparation and antibacterial agents containing them as active ingredients.

2. Description of the Prior Art

A number of cephalosporin compounds have been synthesized which have a 2-(2-aminothiazol-4-yl)-2-substituted oxyiminoacetamido group as a side chain at the 7-position of the cephalosporin nucleus. As publications which disclose such compounds, Japanese Unexamined Patent Publications No. 102293/1977, No. 116492/1977, No. 137988/1978, No. 9296/1979, No. 154786/1979, No. 157596/1979, No. 154980/1980, No. 86187/1981, No. 59895/1982, No. 99592/1982, No. 192394/1982 and No. 174387/1983, may be mentioned. It is suggested that such compounds exhibit activities against Gram-positive bacteria and cephalosporin resistant Gram-negative bacteria including *Pseudomonas aeruginosa*, and they have excellent antibacterial activities and a broad antibacterial spectrum. However, few of them are substantially active against glucose non-fermentative Gram-negative rods, such as *Pseudomonas aeruginosa*, *Pseudomonas cepacia*, *Pseudomonas maltophilia* and *Acinetobacter calcoaceticus*.

Further, Japanese Unexamined Patent Publications No. 57386/1983 and No. 130294/1989 disclose compounds having an isoquinoliniomethyl group at the 3-position of the cephem nucleus. Japanese Unexamined Patent Publication No. 57386/1983 discloses unsubstituted and mono-substituted isoquinoliniomethyl groups. A number of substituents are mentioned. However, so long as a hydroxyl group is concerned, only a 5-OH derivative and a 8-OH derivative have been synthesized. Japanese Unexamined Patent Publication No. 130294/1984 discloses that the isoquinoline nucleus may have a number of substituents. However, only the 5-OH derivative has been practically synthesized. With respect to the hydroxyl group-substituted compounds, these prior art references give merely general statements, and no data on the antibacterial activities are given. Further, there is no disclosure which teaches that the isoquinoline ring may have two hydroxyl groups, and there is no suggestion at all about 6,7-dihydroxy derivatives having adjacent hydroxyl groups.

Since β-lactam antibiotics exhibit selective toxicity only against bacteria and present no substantial effects against animal cells, they have been widely used as antibiotics having no substantial side effects for the treatment of infectious diseases caused by bacteria, and thus they are highly useful drugs.

However, in recent years, glucose non-fermentative Gram-negative rods, particularly *Pseudomonas aeruginosa* have been frequently isolated as causative organisms of refractory infections from immuno-compromized patient, which has posed a serious problem. Therefore, it is desired and beneficial as well to provide antimicrobial agents with improved activity against such bacteria.

SUMMARY OF THE INVENTION

It is an object of the present invention to provide novel cephalosporin derivatives having excellent antibacterial activities.

As a result of an extensive research, it has been found that novel cephalosporin derivatives having a 6,7-dihydroxyisoquinoliniomethyl group or a 6,7-diacetoxyisoquinoliniomethyl group at the 3-position and a 2-(2-aminothiazol-4-yl)-2-substituted oxyiminoacetamido group at the 7-position, have strong antibacterial activities against Gram-negative bacteria particularly glucose non-fermentative Gram-negative rods, such as *Pseudomonas aeuginosa*, *Pseudomonas cepacia*, *Pseudomonas maltophilia*, and *Acinetobacter calcoaceticus* as compared with a compound having a non-substituted isoquinoline nucleus and with a monohydroxy compound, and they have excellent stability against β-lactamase and a low β-lactamase-inducibility. The present invention has been accomplished on the basis of these discoveries.

Namely, the present invention has been accomplished on the basis of the discoveries such that the compounds of the present invention having hydroxyl groups or acetoxy groups at the 6- and 7-positions of the isoquinoline nucleus in the isoquinoliniomethyl group at the 3-position of the cephem nucleus are new compounds not disclosed in any literature, and that they have unexpectedly high antibacterial activities particularly against infectious resistant Gram-negative bacteria as compared with a compound wherein the isoquinoline nucleus is unsubstituted (the compounds of Reference Examples 1 and 2 correspond to compounds of Examples 57 and 36 of Japanese Unexamined Patent Publication No. 130294/1984 respectively; the compounds of Reference Examples 2 and 3 correspond to compounds of Examples 7 and 6 of Japanese Unexamined Patent Publication No. 57386/1983 respectively) and they have excellent stability against β-lactamase.

The present invention provides a compound having the formula:

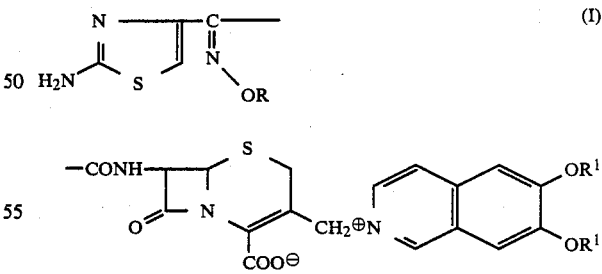

wherein R is a straight chain, branched chain or cyclic lower alkyl, lower alkenyl or lower alkynyl group which may be substituted by a carboxyl group, and $R^1$ is a hydrogen atom or an acetyl group; or a pharmaceutically acceptable salt, physiologically hydrolyzable ester or solvate thereof.

Further, the present invention provides a process for preparing the compound of the formula I, which comprises reacting a compound having the formula:

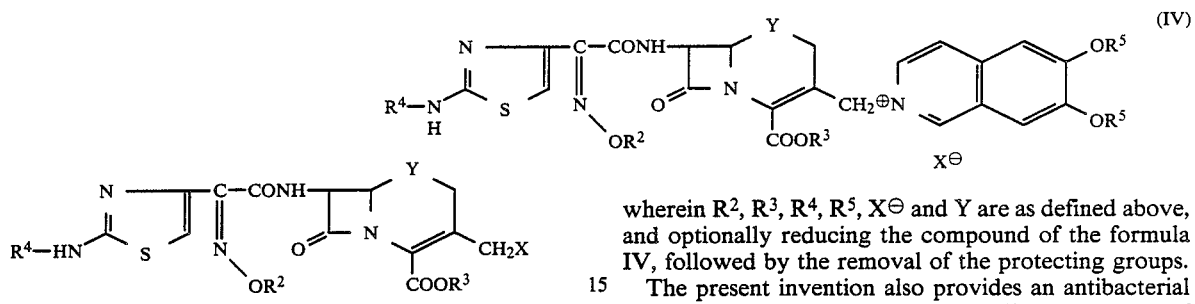

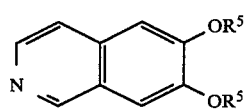

wherein $R^2$ is a straight chain, branched chain or cyclic lower alkyl, lower alkenyl or lower alkynyl group which may be substituted by a protected carboxyl group, $R^3$ is a hydrogen atom or a carboxyl-protecting group, $R^4$ is a hydrogen atom or an amino-protecting group, X is a leaving group, any Y is S or SO, or a salt thereof, with an amine having the formula:

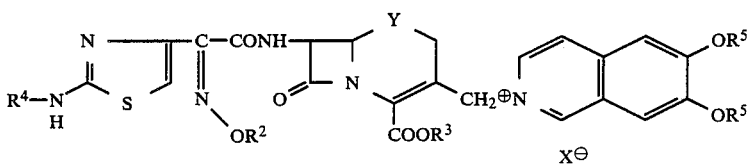

wherein $R^5$ is a hydrogen atom or a hydroxyl-protecting group, to form a compound having the formula:

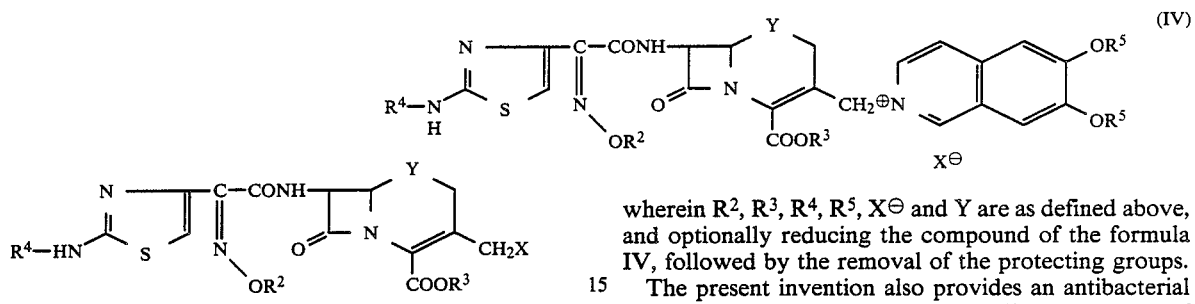

wherein $R^2$, $R^3$, $R^4$, $R^5$ and Y are as defined above, and $X^\ominus$ is an anion, and optionally reducing the compound of the formula IV, followed by the removal of the protecting groups.

Another process of the preparation of the compound of the formula I, comprises acylating a compound having the formula:

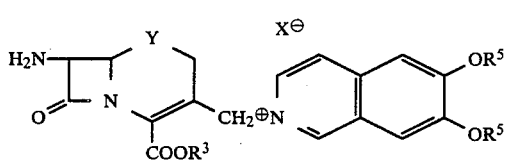

wherein $R^3$ is a hydrogen atom or a carboxyl-protecting group, $R^5$ is a hydrogen atom or a hydroxyl-protecting group, $X^\ominus$ is an anion, and Y is S or SO, or a salt thereof, with a reactive derivative of a carboxylic acid having the formula:

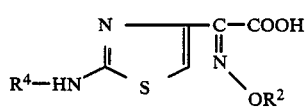

wherein $R^2$ is a straight chain, branched chain or cyclic lower alkyl, lower alkenyl or lower alkynyl group which may be substituted by a protected carboxyl group, and $R^4$ is a hydrogen atom or an amino-protecting group, to form a compound having the formula:

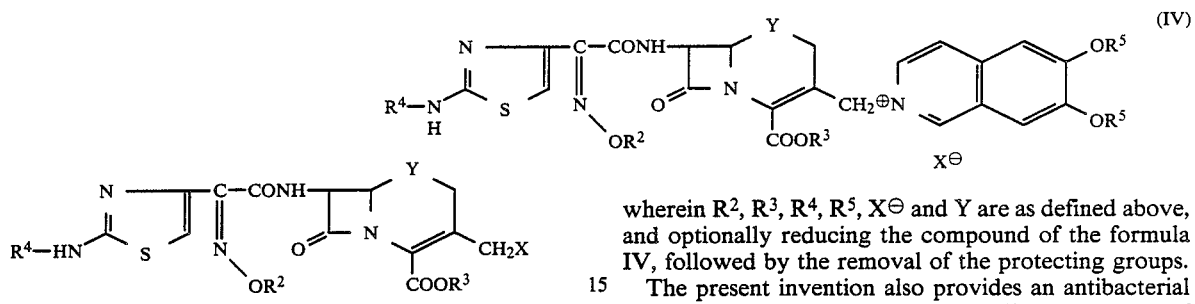

wherein $R^2$, $R^3$, $R^4$, $R^5$, $X^\ominus$ and Y are as defined above, and optionally reducing the compound of the formula IV, followed by the removal of the protecting groups.

The present invention also provides an antibacterial agent comprising an antibacterially effective amount of the compound of the formula I and a pharmaceutically acceptable carrier.

DETAILED DESCRIPTION OF THE PREFERRED EMBODIMENTS

Now, the symbols and terms used in the present specification will be explained.

The substituent R in the compound of the formula I represents a straight chain or branched chain lower alkyl, lower alkenyl or lower alkynyl, or cyclic lower alkyl group, which may be substituted by a carboxyl group. The straight chain or branched chain lower alkyl group includes alkyl groups having from 1 to 6 carbon atoms, such as methyl, ethyl, n-propyl, isopropyl, n-butyl, isobutyl, sec-butyl, t-butyl, n-pentyl and n-hexyl.

Particularly preferred are, for example, methyl, ethyl, n-propyl and isopropyl. The lower alkenyl group includes alkenyl groups having from 2 to 6 carbon atoms such as vinyl, allyl, isopropenyl, 1,1-dimethylallyl, 2-butenyl and 3-butenyl. The lower alkynyl group includes alkynyl groups having from 2 to 3 carbon atoms, such as ethynyl and 2-propynyl. The cyclic lower alkyl group includes cyclopropyl, cyclobutyl, cyclopentyl and cyclohexyl. As preferred examples of the substituent R containing a carboxyl group as a substituent, there may be mentioned carboxymethyl, 1-carboxy-1-methylethyl, 1-carboxy-1-cyclopropyl, 1-carboxy-1-cyclobutyl, 1-carboxy-1-cyclopentyl, 1-carboxyvinyl, 1-carboxyallyl, 2-carboxyallyl, 1-carboxymethylvinyl, 2-carboxyethynyl, 1-carboxy-2-propynyl and 3-carboxy-2-propynyl.

6,7-Dihydroxyisoquinoline and 6,7-diacetoxyisoquinoline are novel compounds not disclosed in literatures. Cephalosporin derivatives having a 6,7-dihydroxyisoquinoliniomethyl group or a 6,7-diacetoxyisoquinoliniomethyl group at the 3-position of the cephem nucleus have not previously synthesized.

The compound of the formula II of the present invention having a 6,7-dihydroxyisoquinoliniomethyl group at the 3-position of a cephalosporin nucleus, has the following feature.

In this specification, the structure of the 6,7-dihydroxyisoquinolinio group in the formula I is represented by the following formula A for the convenience sake.

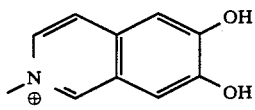 (A)

However, the formula A has a tautomer attributable to the 6,7-dihydroxyisoquinoline nucleus and may also be represented by the formula A'.

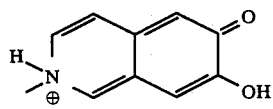 (A')

Namely, the compounds of the formulas A and A' are in an equilibrium condition of tautomerism whereby they are tautomerizable to each other depending upon the state of the compounds (e.g. solid or liquid), the type of the solvent, the nature of the solution, the temperature, etc. Thus, both of such tautomers are within the scope of the present invention.

Further, the moiety

in the oxyimino group in the formula I, includes a syn-isomer (Z configuration:

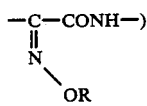

and an anti-isomer (E configuration:

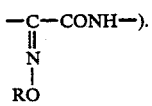

Generally, the syn-isomer (Z configuration) exhibits superior antibacterial activities. In this specification, the OR group represents the syn-isomer (Z configuration) in all cases. The nomenclature for E and Z configurations is described in Journal of the American Chemical Society, Vol. 90, p 509 (1968).

The compounds of the formula I may be converted to non-toxic salts or physiologically hydrolyzable non-toxic esters thereof by usual methods. The non-toxic salts of the compounds of the formula I mean pharmaceutically acceptable usual salts. For instance, a salt of a metal such as sodium, potassium, calcium, magnesium or aluminum, a salt of an organic amine such as N,N'-dibenzylethylenediamine or procaine, a salt of an inorganic acid such as hydrochloric acid, hydrobromic acid, nitric acid, sulfuric acid or perchloric acid, a salt of an organic acid such as acetic acid, lactic acid, propionic acid, maleic acid, fumaric acid, malic acid, tartaric acid or citric acid, a salt of a sulfonic acid such as methanesulfonic acid, isethionic acid or p-toluenesulfonic acid and a salt of an amino acid such as glutamic acid, aspartic acid, lysine or arginine, may be mentioned.

The non-toxic esters of the compounds of the formula I mean pharmaceutically acceptable usual esters of the carboxyl groups thereof. For instance, an alkanoyloxymethyl group such as an acetoxymethyl group or a pivaloyloxymethyl group, an alkoxycarbonyloxyalkyl group such as a 1-(ethoxycarbonyloxy)ethyl group, a phthalidyl group, and a 5-substituted-2-oxo-1,3-dioxol-4-ylmethyl group such as a 5-methyl-2-oxo-1,3-dioxol-4-ylmethyl group, may be mentioned.

Now, the processes for the preparation of the compounds of the present invention will be described.

The compound of the formula I may be prepared by either one of the following processes A and B.

Process A

The compound of the formula I of the present invention can be prepared by reacting a compound having the formula:

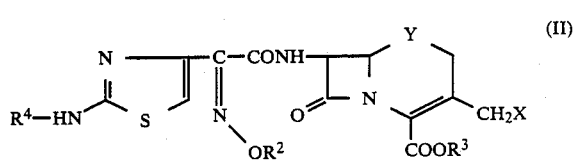 (II)

wherein $R^2$ is a straight chain, branched chain or cyclic lower alkyl, lower alkenyl or lower alkynyl group which may be substituted by a protected carboxyl group, $R^3$ is a hydrogen atom or a carboxyl-protecting group, $R^4$ is a hydrogen atom or an amino-protecting group, X is a leaving group, and Y is S or SO, or a salt thereof, with an amine having the formula:

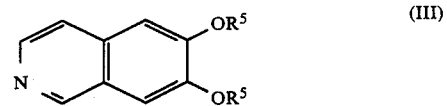 (III)

wherein $R^5$ is a hydrogen atom or a hydroxyl-protecting group, to form a compound having the formula:

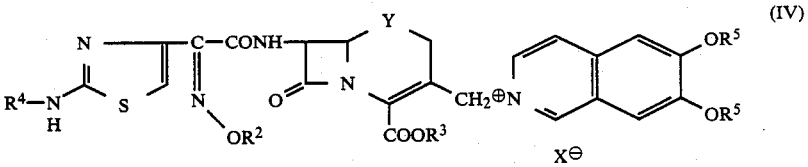 (IV)

wherein $R^2$, $R^3$, $R^4$, $R^5$ and Y are as defined above, and $X^\ominus$ is an anion, and optionally reducing the compound of the formula IV, followed by the removal of the protecting groups.

The substituent X in the formula II represents a leaving group. Specifically, there may be mentioned a halogen atom such as chlorine, bromine or iodine, an acetoxy group, a carbamoyloxy group, a trifluoromethanesulfonyloxy group and a p-toluenesulfonyloxy group. Particularly preferred is a bromine atom, an iodine atom or an acetoxy group.

The 6,7-dihydroxyisoquinoline and 6,7-diacetoxyisoquinoline represented by the formula III, are novel compounds, and the hydroxyl groups may be protected.

Process B

The compound of the formula I of the present invention can also be prepared by acylating a compound having the formula:

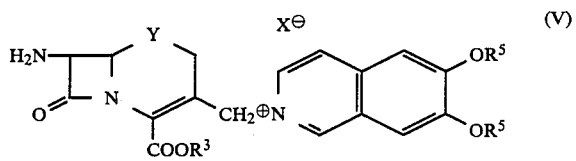

wherein $R^3$ is a hydrogen atom or a carboxyl-protecting group, $R^5$ is a hydrogen atom or a hydroxyl-protecting group, $X^\ominus$ is an anion, and Y is S or SO, or a salt thereof, with a reactive derivative of a carboxylic acid having the formula:

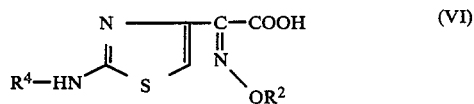

wherein $R^2$ is a straight chain, branched chain or cyclic lower alkyl, lower alkenyl or lower alkynyl group which may be substituted by a protected carboxyl group, and $R^4$ is a hydrogen atom or an amino-protecting group, to form a compound having the formula:

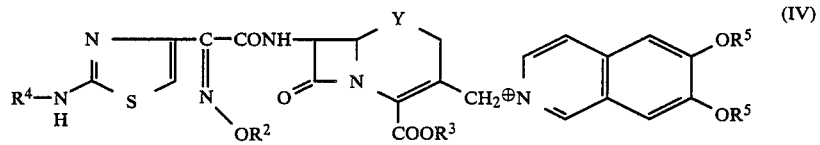

wherein $R^2$, $R^3$, $R^4$, $R^5$, $X^\ominus$ and Y are as defined above, and optionally reducing the compound of the formula IV, followed by the removal of the protecting groups.

Further, a compound of the present invention having a 6,7-diacetoxyisoquinoliniomethyl group may be prepared by conducting a condensation reaction of the compound of the formula III wherein $R^5$ is an acetyl group with the compound of the formula II or its salt, or acylating the compound of the formula V or its salt wherein $R^5$ is an acetyl group with a reactive derivative of a carboxylic acid of the formula VI and optionally reducing the resulting product of the formula IV or removing the protective groups. Furthermore, it may also be produced by selectively acetylating a compound of the formula I having a 6,7-dihydroxyisoquinoliniomethyl group under suitable conditions.

As the protecting groups for the carboxyl, amino and hydroxyl groups in the above formulas, protecting groups which are commonly employed in the field of β-lactam synthesis, may suitably be selected for use. As the carboxyl-protecting group, there may be mentioned t-butyl, 2,2,2-trichloroethyl, acetoxymethyl, propionyloxymethyl, pivaloyloxymethyl, 1-acetoxyethyl, 1-propionyloxyethyl, 1-(ethoxycarbonyloxy)ethyl, phthalidyl, benzyl, 4-methoxybenzyl, 3,4-dimethoxybenzyl, 4-nitrobenzyl, benzhydryl, bis(4-methoxyphenyl)methyl, 5-methyl-2-oxo-1,3-dioxol-4-ylmethyl, trimethylsilyl and t-butyldimethylsilyl. Particularly preferred are benzhydryl, t-butyl and silyl.

As the amino-protecting group, there may be mentioned, for example, trityl, formyl, chloroacetyl, trifluoroacetyl, t-butoxycarbonyl, trimethylsilyl and t-butyldimethylsilyl.

As the hydroxyl-protecting group, there may be mentioned, for example, 2-methoxyethoxymethyl, methoxymethyl, methylthiomethyl, tetrahydropyranyl, phenacyl, isopropyl, t-butyl, benzyl, 4-nitrobenzyl, acetyl, 2,2,2-trichloroethoxycarbonyl, benzyloxycarbonyl, acetonide, trimethylsilyl and t-butyldimethylsilyl.

Now, processes A and B for the preparation of the compounds of the formula I of the present invention, will be described in detail.

Process A

The reaction of the compound of the formula II with the 6,7-di-substituted isoquinoline of the formula III, may be conducted in an organic solvent such as methylene chloride, chloroform, ethyl ether, ethyl acetate, butyl acetate, tetrahydrofuran, acetonitrile, N,N-dimethylformamide or dimethylsulfoxide, or in a mixture of such solvents. The di-substituted isoquinoline of the formula III may be employed in the form of its acid addition salt such as hydrochloride, hydrobromide, sulfate, nitrate, formate or acetate. In such a case, this reaction is conducted in the presence of an acid-absorbing agent such as triethylamine, diisopropylethylamine, N,N-dimethylaniline or N-methylmorpholine in an amount sufficient for neutralization. Further, the di-substituted isoquinoline of the formula III may be employed in a form silylated with a silylating agent such as N,O-bistrimethylsilylacetoamide. The reaction is conducted by using from 1 to 2 mols of the di-substituted isoquinoline of the formula III relative to 1 mol of the compound of the formula II. The reaction temperature and the reaction time are from 0° to 40° C. and from 0.5 to 5 hours, respectively.

The reaction of a compound of the formula II wherein X is an acetoxy group, with the di-substituted isoquinoline of the formula III, may be conducted in a solvent such as water, a phosphoric acid buffer solution, acetone, acetonitrile, methanol, ethanol, tetrahydrofuran, dioxane, N,N-dimethylformamide or dimethylsulfoxide, in a mixture of such solvents. The reaction is preferably conducted under a neutral condition. The reaction temperature is from room temperature to 90° C., and the reaction time is from 1 to 10 hours. The reaction is facilitated by conducting it in the presence of an iodide such as sodium iodide or potassium iodide, or a thiocyanate such as sodium thiocyanate or potassium thiocyanate.

The sulfoxide group of an ammonio compound of the formula IV wherein Y is SO, may be reduced by a method described in e.g. Journal of Organic Chemistry, Vol. 35, p 2430 (1974). Namely, the ammonio compound of the formula IV wherein Y is SO may be reduced by reacting it in acetone as a solvent in the presence of sodium iodide or potassium iodide with a dropwise addition of acetyl chloride at a temperature of from −40° to 0° C. for from 1 to 5 hours. The reaction is conducted by using from 3.5 to 10 mols of the iodide and from 1.5 to 5 mols of acetyl chloride relative to 1 mol of the compound of the formula IV wherein Y is SO.

The compound of the formula I of the present invention may be prepared, if necessary, by removing the protecting groups from the compound of the formula IV wherein Y is S. The removal of the protecting groups may be conducted by employing a suitable method selected, for instance, from those described in Protective Groups in Organic Synthesis (1981) written by T. W. Greene. For instance, the removal of a protecting group such as trityl, formyl, t-butoxycarbonyl, benzhydryl, t-butyl or 2-methoxyethoxymethyl, may be conducted with an inorganic or organic acid such as hydrochloric acid, formic acid, trifluoroacetic acid, benzenesulfonic acid or p-toluenesulfonic acid. Trifluoroacetic acid is particularly preferred.

When trifluoroacetic acid is used as the acid, the reaction can be facilitated by an addition of anisole, and side reactions can be thereby suppressed.

The reaction may be conducted in a solvent which is inert to the reaction, such as water, methylene chloride, chloroform, ethylene chloride or benzene, or in a mixture of such solvents. The reaction temperature and time are suitably selected depending upon the chemical properties of the compound of the formula IV and the compound of the formula I of the present invention and the type of the protecting group to be removed. The reaction is preferably conducted under a condition ranging from an ice-cooling condition to a slightly heated condition.

The starting compound of the formula II for process A may be prepared in the following manner. The compound of the formula II wherein Y is S can be prepared by reacting benzhydryl 7-amino-3-chloromethyl-3-cephem-4-carboxylate (synthesized in accordance with e.g. Japanese Unexamined Patent Publications No. 76089/1975 and No. 86187/1981), 7-aminocephalosporic acid or its ester, with a carboxylic acid of the formula VI or its reactive derivative (such as its acid halide, mixed acid anhydride, activated ester, etc.).

A compound of the formula II wherein Y is SO can be prepared by oxidizing a compound of the formula II wherein Y is S with a stoichiometric amount of m-chloroperbenzoic acid in an organic solvent inert to the reaction such as methylene chloride, ethylene chloride or chloroform, under cooling with ice.

A compound of the formula II wherein X is an iodine atom, can be prepared by reacting a compound of the formula II wherein X is a chlorine atom, with an iodide such as sodium iodide in a solvent such as acetone or N,N-dimethylformamide, under cooling with ice or at room temperature, and the product may be used for the subsequent reaction without or after isolation.

The 6,7-disubstituted quinoline of the formula III can be prepared by the acid hydrolysis of 6,7-dimethoxyisoquinoline synthesized by the method disclosed in e.g. Journal of the American Chemical Society, Vol. 79, p 3773 (1957) or J. Chem. Soc. Perkin, 1., p 2185 (1974) and p 2190 (1974), or by the catalytic reduction of a 6,7-bis(benzyloxy)isoquinoline.

The 2-(2-substituted aminothiazol-4-yl)-2-substituted oxyiminoacetic acid of the formula VI, can be prepared by a method disclosed in e.g. Japanese Unexamined Patent Publication No. 149289/1980.

Process B

The compound of the formula IV may be prepared by reacting the compound of the formula V with the carboxylic acid of the formula VI or its reactive derivative (such as its acid halide, mixed anhydride or activated ester) in a solvent inert to the reaction such as water, acetone, dioxane, acetonitrile, tetrahydrofuran, methylene chloride, chloroform, ethylene chloride, benzene, ethyl acetate, N,N-dimethylformamide or dimethylsulfoxide, or in a mixture of such solvents.

The reaction is conducted by using from 1 to 1.5 mols of the carboxylic acid of the formula VI or its reactive derivative relative to 1 mol of the compound of the formula V, and the reaction temperature is from −40° to 40° C.

When an acid halide is used as the reactive derivative of the formula VI, the reaction is preferably conducted in the presence of an acid-absorbing agent such as triethylamine, N-methylmorpholine, N,N-dimethylaniline or pyridine.

The acid halide-forming reaction is carried out by using from 1 to 10 mols, preferably from 1 to 1.5 mols of the halogenating agent such as thionyl chloride, phosphorus trichloride, phosphorus tribromide, phosphorus pentachloride, phosphorus oxychloride, oxalylchloride or phosgene, at a reaction temperature of from −40° to 100° C., preferably from −20° to 20° C. for a reaction time of a few hours.

The mixed acid anhydride-forming reaction is conducted by using from 1 to 1.2 mols of a chloroformate such as methyl chloroformate, ethyl chloroformate or isobutyl chloroformate in the presence of from 1 to 1.2 mols of an acid-absorbing agent such as triethylamine, N-methylmorpholine, N,N-dimethylaniline or pyridine, relative to 1 mol of the carboxylic acid of the formula VI. The reaction temperature is from −40° to 20° C., preferably from −20° to 5° C. The reaction time is from 10 to 60 minutes.

The active ester-forming reaction is conducted by using from 1 to 1.2 mols of a N-hydroxy compound (such as N-hydroxysuccinimide or 1-hydroxybenzotriazole) or a phenol compound (such as 4-nitrophenol, 2,4-dinitrophenol or trichlorophenol) and from 1 to 1.4 mols of N,N'-dicyclohexylcarbodiimide, relative to 1 mol of the carboxylic acid of the formula VI. The reaction temperature is from −10° to 50° C. The reaction time is from 0.5 to 2 hours.

When the carboxylic acid of the formula VI is used in the form of a free acid in the acylation reaction, the compound of the formula IV may be prepared in the presence of a condensation agent such as a carbodiimide such as N,N'-dicyclohexylcarbodiimide, or phosphorus oxychloride, an phosphorus oxychloride adduct of N,N-dimethylformamide. The preparation of the compound of the formula I of the present invention from the compound of the formula IV, is substantially the same as in process A.

The starting compound of the formula V in process B, may be prepared by a method disclosed in e.g. Cephalosporins and Penicillins, Academic Press, p 151–171, (1972) written by Lynn. For instance, a 7-acylamino-3- halomethyl-3-cephem-4-carboxylate derivative (Japanese Unexamined Patent Publication No. 72590/1983 or No. 154588/1983) or a 7-acylamino cephalosporanic acid derivative, is reacted with the 6,7-di-substituted isoquinoline of the formula III to obtain a compound having the formula:

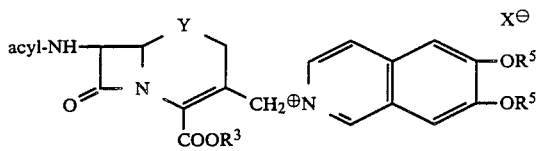

wherein $R^3$ is a hydrogen atom or a carboxyl-protecting group, $R^5$ is a hydrogen atom or a hydroxyl-protecting group, Y is S or SO, $X^\ominus$ is an anion as a leaving group, and acyl is an acyl group, followed by deacylation.

The deacylation reaction is commonly known in this field. For instance, there may be mentioned a method comprising iminochlorination with e.g. phosphorus pentachloride, followed by iminoetherification and hydrolysis with e.g. methanol, or a method using an acylase.

As the acyl group, for instance, a phenylacetyl group, a phenoxyacetyl group or an aminoadipyl group may be mentioned.

The in vitro antibacterial activities of the compounds of the present invention against various microorganisms, were measured by the following agar plate dilution method. One platinum loopfull of each test microorganism incubated overnight in Mueller Hinton broth, was inoculated to Mueller Hinton agar (inoculum size: $10^6$ CFU/ml). Such culture media containing various antibiotics in various concentrations were prepared. After incubation at 37° C. for 16 hours, the minimum inhibitory concentrations (MIC: μg/ml) were measured. As comparative compounds, Cefotaxime, Ceftazidime and the compounds of Reference Examples 1 to 4 were employed. The results are shown in the following table.

TABLE

| Test microorganism | Minimum Inhibitory Concentration (MIC: μg/ml) | | | | | | | |
| --- | --- | --- | --- | --- | --- | --- | --- | --- |
| | Compound of Ex. 1 | Compound of Ex. 2 | Compound of Ex. 3 | Compound of Ex. 4 | Compound of Ex. 5 | Compound of Ex. 6 | Compound of Ex. 7 | Compound of Ex. 8 |
| 1. S. aureus 209P NIHJ-JC1 | 1.56 | 1.56 | 0.78 | 25 | 25 | 25 | 1.56 | 6.25 |
| *2. S. aureus JS1 | 25 | 12.5 | 12.5 | 100 | 100 | 100 | 50.0 | 50.0 |
| 3. S. aureus BB5703 | 3.12 | 6.25 | 6.25 | 50 | 50 | 50 | 6.25 | 12.5 |
| 4. S. epidermidis IAM12012 | 0.78 | 0.78 | 0.39 | 12.5 | 6.25 | 12.5 | 0.200 | 3.12 |
| 5. M. luteus ATCC9341 | 0.10 | 0.10 | 0.20 | 6.25 | 3.12 | 6.25 | 0.200 | 0.780 |
| 6. C. freundii GN346/16 | 0.78 | 0.78 | 0.39 | 1.56 | 1.56 | 1.56 | 0.780 | 0.780 |
| 7. E. coli NIHJ JC2 | 0.05 | 0.10 | 0.10 | 0.10 | 0.05 | 0.10 | 0.200 | 0.100 |
| *8. E. coli CSH2 (RK1) | <0.006 | <0.006 | 0.0125 | <0.006 | 0.0125 | 0.0125 | <0.006 | 0.0125 |
| 9. K. pneumoniae PCI-602 | <0.006 | <0.006 | <0.006 | <0.006 | <0.006 | <0.006 | <0.006 | <0.006 |
| *10. E. coli CSH(RE45) | 0.78 | 0.39 | 0.025 | 0.39 | 0.78 | 0.025 | 0.050 | 0.100 |
| *11. K. oxytoca GN10650 | 0.78 | 0.39 | 3.12 | <0.006 | 0.0125 | 0.05 | 1.56 | 0.200 |
| *12. K. pneumoniae No. 42 | 0.025 | 0.025 | 0.10 | 0.025 | 0.05 | 0.025 | <0.006 | 0.0125 |
| 13. P. vulgaris HX-19 | <0.006 | <0.006 | <0.006 | <0.006 | <0.006 | <0.006 | <0.006 | 0.025 |
| *14. P. vulgaris No. 33 | 0.10 | 0.05 | 0.10 | 0.0125 | 0.0125 | 0.0125 | 0.050 | 0.100 |
| 15. S. marcescens IAM 1184 | 0.0125 | 0.0125 | 0.0125 | 0.0125 | <0.006 | 0.0125 | <0.006 | 0.025 |
| *16. V. freundii GN346 | 25 | 50 | 50 | 50 | 50 | 50 | 50.0 | 50.0 |
| 17. E. cloacae 963 | 0.025 | 0.025 | 0.05 | 0.025 | 0.05 | 0.125 | 0.0125 | 0.025 |
| *18. E. cloacae Nek 39 | 0.10 | 0.05 | 0.10 | 0.025 | <0.006 | 0.025 | 0.200 | 0.200 |
| *19. E. coli GN5482 | 0.39 | 0.39 | 0.39 | 0.39 | 0.20 | 0.20 | 0.780 | 0.780 |
| *20. M. morganii GN5407 | 0.10 | 0.05 | 0.05 | 0.05 | 0.10 | 0.05 | 0.050 | 0.050 |
| *21. S. marcescens No. 16-2 | 3.12 | 0.78 | 1.56 | 0.20 | 0.10 | 0.10 | 1.56 | 1.56 |
| 22. Ps. aeruginosa IFO3445 | 0.78 | 0.78 | 0.39 | 0.20 | 0.39 | 1.56 | 0.780 | 0.780 |
| 23. Ps. aeruginosa AK 109 | 0.78 | 0.78 | 0.78 | 0.20 | 0.39 | 0.39 | 0.780 | 0.780 |
| 24. Ps. aeruginosa AKR17 | 100 | 25 | 100 | 0.78 | 0.39 | 1.56 | 100 | 100 |
| 25. Ps. cepacia 23 | 0.78 | 0.10 | <0.006 | <0.006 | <0.006 | 0.025 | 0.100 | 0.200 |
| *26. Ps. maltophilia GN 12873 | >100 | 100 | >100 | 1.56 | 1.56 | 25 | >100 | >100 |
| 27. A. calcoaceticus No. 4 | 0.20 | 0.20 | 0.20 | 0.10 | 0.10 | 0.20 | 0.200 | 0.200 |

| Test microorganism | Minimum Inhibitory Concentration (MIC: μg/ml) | | | | | |
| --- | --- | --- | --- | --- | --- | --- |
| | Compound of Reference Ex. 1 | Compound of Reference Ex. 2 | Compound of Reference Ex. 3 | Compound of Reference Ex. 4 | Ceftazidime | Cefotaxime |
| 1. S. aureus 209P NIHJ-JC1 | 6.25 | 0.39 | 0.78 | 12.5 | 6.25 | 1.56 |
| *2. S. aureus JS1 | 50 | 6.25 | 25.0 | 100 | 50 | 25 |
| 3. S. aureus BB5703 | 25 | 3.12 | 3.12 | 100 | 25 | 3.12 |
| 4. S. epidermidis IAM12012 | 1.56 | — | — | — | 3.12 | 0.39 |
| 5. M. luteus ATCC9341 | 0.78 | — | — | — | 1.56 | 0.05 |
| 6. C. freundii GN346/16 | 0.20 | 0.10 | 0.10 | 1.56 | 0.20 | 0.10 |
| 7. E. coli NIHJ JC2 | 0.20 | 0.025 | 0.05 | 0.78 | 0.20 | 0.05 |
| *8. E. coli CSH2 (RK1) | 0.05 | 0.025 | 0.025 | 0.39 | 0.10 | 0.05 |
| 9. K. pneumoniae PCI-602 | 0.125 | <0.006 | <0.006 | 0.20 | 0.125 | <0.006 |
| *10. E. coli CSH(RE45) | 0.10 | 1.56 | 0.39 | 0.39 | 0.10 | 0.20 |
| *11. K. oxytoca GN10650 | 0.20 | 12.5 | 3.12 | 0.39 | 0.20 | 0.78 |
| *12. K. pneumoniae No. 42 | 0.39 | 0.10 | 0.10 | 0.78 | 0.39 | 0.05 |
| 13. P. vulgaris HX-19 | 0.0125 | <0.006 | 0.0125 | 0.0125 | 0.025 | <0.006 |
| *14. P. vulgaris No. 33 | 0.10 | 0.10 | 0.05 | 0.10 | 0.05 | 0.025 |
| 15. S. marcescens IAM 1184 | 0.05 | 0.025 | 0.025 | 0.20 | 0.025 | 0.05 |
| *16. V. freundii GN346 | 50 | 6.25 | 12.5 | >100 | 25 | 25 |
| 17. E. cloacae 963 | 0.20 | 0.025 | 0.05 | 0.78 | 0.20 | 0.10 |
| *18. E. cloacae Nek 39 | 1.56 | 0.78 | 0.78 | 12.5 | 1.56 | 3.12 |
| *19. E. coli GN5482 | 0.78 | 0.20 | 0.39 | 6.25 | 3.12 | 0.39 |
| *20. M. morganii GN5407 | 0.05 | 0.025 | 0.025 | 0.10 | 0.10 | 0.05 |

TABLE-continued

|    | | | | | | | |
|---|---|---|---|---|---|---|---|
| *21. | S. marcescens No. 16-2 | 1.56 | 3.12 | 3.12 | 6.25 | 1.56 | 25 |
| 22. | Ps. aeruginosa IFO3445 | 3.12 | 3.12 | 12.5 | 6.25 | 0.39 | 3.12 |
| 23. | Ps. aeruginosa AK 109 | 3.12 | 3.12 | 50 | 6.25 | 1.56 | 12.5 |
| 24. | Ps. aeruginosa AKR17 | 100 | >100 | >100 | >100 | >100 | >100 |
| 25. | Ps. cepacia 23 | 6.25 | 6.25 | 6.25 | 1.56 | 1.56 | 6.25 |
| *26. | Ps. maltophilia GN 12873 | 12.5 | >100 | >100 | 50 | 100 | >100 |
| 27. | A. calcoaceticus No. 4 | 25 | 12.5 | 25 | 25 | 6.25 | 25 |

*β-Lactamase-producing strains

Thus, the compounds of the present invention exhibit strong antibacterial activities against sensitive and resistant Gram-negative bacteria particularly glucose non-fermentative Gram-negative rods, such as Pseudomonas aeruginosa, Pseudomonas cepacia, Pseudomonas maltophilia, and Acinetobacter calcoaceticus.

Further, with respect to the compound of Example 4, the β-lactamase-inducibility activity was measured by *Enterobacter cloacae* GN 5797, whereby no substantial β-lactamase-inducing activity was observed. The assay method for induction of β-lactamase by β-lactam antibiotics was as follows:

The test organism, *Enterobacter cloacae* GN 5797, was grown overnight in Mueller Hinton broth (Dlfco Laboratories, Detroit, Mich.) at 37° C. The culture was diluted 10-fold into 20 ml of the flesh medium and incubated with shaking at 37° C. After 2 hours of incubation, antibiotics were added to final concentrations of 50 μg/ml, 10 μg/ml and 1 μg/ml, and the incubation was continued. At 1 hour intervals after the addition of antibiotic, 3 ml of sample was taken, and immediately added with 0.1 ml of 50 mM sodium azide. The cells were harvested and washed with 50 mM phosphate buffer (pH 7.0). The cells were suspended in 50 ml of 50 mM phosphate buffer and disrupted with a sonicater in an ice-water bath. The broken cells were centrifuged at 16,500G for 40 minutes at 4° C., and the resulting supernatant fluid was used as the crude enzyme. β-Lactamase activity was determined by a spectrophotometric method (Antimicrob. Agents Chemother. 17, 355–358, 1980) with cephaloridine as substrate. The concentration of protein was determined by the method of Lowry (J. Biol. Chem. 193, 265–275, 1951).

| Test compound | Concentration (μg/ml) | Incubation time (hr) | Specific activity (unit/mg protein) |
|---|---|---|---|
| Compound of Example 4 | 10 | 3 | 0.064 |
| Cefoxitin | 10 | 3 | 0.238 |

(Substrate: 100 μM of cephaloridine)

Thus, the compounds of the formula I and non-toxic salts and physiologically hydrolyzable non-toxic esters thereof are useful as antibacterial agents.

The compounds of the present invention may be mixed with a carrier of solid or liquid excipient, and may be used in the form of a pharmaceutical formulation suitable for parenteral administration, oral administration or external administration. As the pharmaceutical formulations, there may be mentioned liquid formulations such as injection solutions, syrups and emulsions, solid formulations such as tablets, capsules and granules and formulations for external application such as ointments and suppositories. Further, these formulations may contain commonly employed additives such as assisting agents, stabilizers, wetting agents, emulsifying agents, absorption-promoting agents or surfactants. As such additives, distilled water for injection, a Ringer solution, glucose, sucrose syrup, gelatin, edible oil, coconut oil, ethylene glycol, sucrose, corn starch, magnesium stearate and talc, may be mentioned.

Further, the compounds of the present invention can be used as antibacterial agents for the treatment of infections diseases caused by Gram-negative bacteria including glucose non-fermentative Gram-negative rods such as Pseudomonas aeruginosa, Pseudomonas cepacia, Pseudomonas maltophilia, and Acinetobacter calcoaceticus. The dose may vary depending upon the age, sex and condition of the patient, and is usually within a range of from 1 to 100 mg/kg per day. It is preferred to administer a daily dose of from 1 to 50 mg/kg in 2 to 5 times.

Now, the present invention will be described in further detail with reference to Examples. However, it should be understood that the present invention is by no means restricted to these specific Examples.

EXAMPLE 1

Preparation of 7-[2-(2-aminothiazol-4-yl)-2-methoxyiminoacetoamido]-3-(6,7-dihydroxyisoquinolinio)-methyl-3-cephem-4-carboxylate (syn-isomer)

(A) 6.35 ml (68 mmol) of phosphorus oxychloride was added to 20 ml of dry ethyl acetate. 5.28 ml (68 mmol) of N,N-dimethylformamide was dropwise added thereto at 0° C., and the mixture was stirred at the same temperature for 15 minutes. To this solution, 180 ml of dry methylene chloride was added. 25.2 g (57 mmol) of 2-methoxyimino-2-(2-tritylaminothiazol-4-yl)acetic acid (syn-isomer) was added thereto at 0° C., and the mixture was stirred for 30 minutes. Then, to this solution, 23.6 g (57 mmol) of benzhydryl 7-amino-3-chloromethyl-3-cephem-4-carboxylate was added, and the mixture was stirred at 0° C. for 2 hours. The reaction solution was adjusted to pH 7.0, and insoluble substances were filtered off. The filtrate was washed sequentially with a 5% sodium hydrogen carbonate aqueous solution and a saturated sodium chloride aqueous solution, then dried over anhydrous sodium sulfate and concentrated under reduced pressure to obtain 44.5 g (yield: 99%) of benzhydryl 3-chloromethyl-7-[2-methoxyimino-2-(2-tritylaminothiazol-4-yl)acetamido]-3-cephem-4-carboxylate (syn-isomer).

IR(KBr) cm$^{-1}$: 1780, 1720, 1670, 1520

NMR(DMSO-d$_6$) δ: 3.67(2H, br s), 3.85(3H, s), 4.45(2H, br s), 5.25(1H, d, J=4.5 Hz), 5.80(1H, m), 6.77(1H, s), 7.00(1H, s), 7.10–7.70(25H, m), 8.80(1H, m), 9.60(1H, m)

(B) 2.5 g (2.97 mmol) of the compound obtained in the above step (A), was dissolved in 25 ml of benzene, and 640 mg (3.27 mmol) of m-chloroperbenzoic acid was added under cooling with ice. The mixture was stirred at room temperature for 1 hour. The reaction solution was poured into ice water, and extracted with ethyl acetate. The extract was washed with a 5% acidic sodium sulfite aqueous solution and a saturated sodium chloride aqueous solution, then dried over anhydrous sodium sulfate and concentrated under reduced pressure to obtain powdery benzhydryl 3-chloromethyl-7-[2-methoxyimino-2-(2-tritylaminothiazol-4-yl)acetamido]-3-cephem-4-carboxylate 1-oxide (syn-isomer).

NMR(CDCl$_3$) δ: 3.25 and 3.70(2H, ABq, J=18 Hz), 4.03(3H, s), 4.13 and 4.70(2H, ABq, J=12 Hz), 4.47(1H, d, J=5 Hz), 6.07(1H, dd, J=5 and 9 Hz), 6.67(1H, s), 6.92(1H, s), 7.30(27H, m)

(C) The compound obtained in the above step (B) was dissolved in 50 ml of acetone, and 670 mg (4.47 mmol) of sodium iodide was added. The mixture was stirred at room temperature for 30 minutes. The reaction solution was poured into ice water, and extracted with ethyl acetate. The extract was washed with a 5% sodium thiosulfate aqueous solution, water and a saturated sodium chloride aqueous solution, then dried over anhydrous sodium sulfate and concentrated under reduced pressure to obtain powdery benzhydryl 3-iodomethyl-7-[2-methoxyimino-2-(2-tritylaminothiazol-4-yl)acetamido]-3-cephem-4-carboxylate 1-oxide (syn-isomer).

IR(KBr) cm$^{-1}$: 1790, 1720, 1680, 1510, 1370, 1290, 1230, 1160, 1040

NMR(CDCl$_3$) δ: 3.40 and 3.68(2H, ABq, J=18 Hz), 4.03(3H, s), 4.48(1H, d, J=5 Hz), 6.00(1H, dd, J=5 and 9 Hz), 6.67(1H, s), 6.95(1H, s), 7.30(27H, m)

(D) 1.0 g (1.1 mmol) of the compound obtained in the above step (C) and 300 mg (1.15 mmol) of 6,7-dihydroxyisoquinoline hydrobromide monohydrate, were dissolved in 5 ml of dry N,N-dimethylformamide, and 0.17 ml (1.2 mole) of triethylamine was dropwise added thereto at room temperature. The mixture was stirred at the same temperature for 2 hours. The reaction solution was concentrated under reduced pressure, and the residue was extracted with chloroform. The organic layer was washed with a saturated sodium chloride aqueous solution, then dried over anhydrous sodium sulfate and concentrated under reduced pressure to obtain 1.0 g (yield: 85%) of benzhydryl 3-(6,7-dihydroxyisoquinolinio)methyl-7-[2-methoxyimine-2-(2-tritylaminothiazol-4-yl)aectamido]-3-cephem-4-carboxylate 1-oxide iodide (syn-isomer).

IR(KBr) cm$^{-1}$: 1800, 1730, 1670, 1630, 1520

NMR(DMSO-d$_6$) δ: 3.50-4.10 (2H, m), 3.82 (3H, s), 5.10 (1H, m), 5.40 (2H, m), 5.95 (1H, m), 6.80 (1H, s), 7.00 (1H, s), 7.05-8.30 (29H, m), 9.03 (1H, s)

(E) 1.0 g (0.9 mmol) of the compound obtained in the above step (D) and 1.5 g (9.0 mmol) of potassium iodide, were suspended in 20 ml of dry acetone, and 0.32 ml (4.5 mmol) of acetyl chloride was dropwise added thereto at −20° C. Then, the mixture was stirred at −10° C. for 3 hours. The reaction solution was poured into 100 ml of a 2% sodium metabisulfite aqueous solution, and the precipitates were collected by filtration and washed with water. The precipitates were dissolved in chloroform, then washed with a saturated sodium chloride aqueous solution, dried over anhydrous sodium sulfate and concentrated under reduced pressure to obtain 1.0 g (yield: 85%) of benzhydryl 3-(6,7-dihydroxyisoquinolinio)methyl-7-[2-methoxyimino-2-(2-tritylaminothiazol-4-yl)acetamido]-3-cephem-4-carboxylate iodide (syn-isomer).

IR(KBr) cm$^{-1}$: 1790, 1730, 1680, 1530

NMR(DMSO-d$_6$) δ: 3.55 (2H, m), 3.80 (3H, s), 5.25 (1H, d, J=4.5 Hz), 5.50 (2H, m), 5.85 (1H, m), 6.70 (1H, s), 6.95 (1H, s), 7.00–7.80 (26H, m), 8.75 (1H, m), 9.50 (2H, m)

(F) 0.9 g (0.82 mmol) of the compound obtained in the above step (E), was dissolved in 7 ml of dry methylene chloride, and 1 ml of anisole was added thereto. Then, 7 ml of trifluoroacetic acid was dropwise added thereto at 0° C. The reaction solution was stirred at the same temperature for 2 hours, and then concentrated under reduced pressure. Ethyl ether was added to the residue, and the precipitates were collected by filtration. The precipitates were dissolved in 200 ml of water, and insoluble substances were removed by filtration. Then, the solution was subjected to reversed phase column chromatography (LC-Sorb, manufactured by Chemco Co.). The fractions containing the desired compound eluted with 4% tetrahydrofuran/water were concentrated and freeze-dried to obtain 105 mg (yield: 23%) of the above-identified compound.

MP: 180° C. (decomposed)

IR(KBr) cm$^{-1}$: 1770, 1620, 1540, 1440

NMR(DMSO-d$_6$) δ: 3.00–3.70 (2H, m), 3.78 (3H, s), 5.13 (1H, d, J=4.5 Hz), 5.72 (3H, m), 6.70 (1H, s), 7.20 (1H, s), 7.50 (1H, s), 7.80 L (1H, m), 8.40 (1H, m), 9.35 (1H, br s), 9.50 (1H, m)

EXAMPLE 2

Preparation of 7-[2-(2-aminothiazol-4-yl)-2-isopropoxyiminoacetamido]-3-(6,7-dihydroxyisoquinolinio)methyl-3-cephem-4-carboxylate (syn-isomer)

(A) 0.41 ml (4.4 mmol) of phosphorous oxychoride was added to 5 ml of ethyl acetate, and 0.35 ml (4.5 mmol) of N,N-dimethylformamide was dropwise added thereto under cooling with ice. Then, the mixture was stirred at room temperature for 15 minutes. To the solution, 20 ml of a methylene chloride solution containing 1.59 g (3.38 mmol) of 2-isopropoxyimino-2-(2-tritylaminothiazol-4-yl)acetic acid (syn-isomer) was added, and the mixture was stirred for 30 minutes. To the reaction solution, 1.4 g (3.37 mmol) of benzhydryl 7-amino-3-chloromethyl-3-cephem-4-carboxylate was added under cooling with ice, and the mixture was stirred for 2 hours. To the reaction solution, 50 ml of ethyl acetate and 20 ml of water were added, and the mixture was adjusted to pH 7.0 with a 5N sodium hydroxide aqueous solution. The organic layer was separated and washed sequentially with a 5% sodium hydrogen carbonate aqueous solution, water and a saturated sodium chloride aqueous solution. The organic layer was dried over anhydrous sodium sulfate and then concentrated under reduced pressure. The oily residue was purified by silica gel column chromatography to obtain 1.94 g (yield: 66%) of benzhydryl 3-chloromethyl-7-[2-isopropoxyimino-2-(2-tritylaminothiazol-4-yl)acetamido]-3-cephem-4-carboxylate (syn-isomer).

NMR(CDDl$_3$) δ: 1.32 (6H, d, J=6 Hz), 3.55 (2H, ABq, J=19 Hz), 4.40 (2H, s), 4.62 (1H, m), 5.07 (1H, d, J=4.5 Hz), 6.00 (1H, dd, J=4.5 and 9 Hz), 6.73 (1H, s), 6.97 (1H, s), 7.20–7.60 (25H, br, s)

(B) 1.94 g (2.2 mmol) of the compound obtained in the above step (A), was dissolved in 20 ml of benzene, and 480 mg (2.8 mmol) of m-chloroperbenzoic acid was added thereto under cooling with ice. The mixture was stirred for 1 hour. To the reaction solution, 50 ml of ethyl acetate was added, then washed sequentially with a 2% sodium metabisulfite aqueous solution and a saturated sodium chloride aqueous solution, dried over anhydrous sodium sulfate and concentrated under reduced pressure to obtain 2.0 g (yield: 100%) of benzyhydryl 3-chloromethyl-7-[2-isopropoxyimino-2-(2-tritylaminothiazol-4-yl)acetamido]-3-cephem-4-carboxylate 1-oxide (syn-isomer).

NMR(DMSO-$d_6$) δ: 1.25 (6H, m), 5.09 (1H, d, J=4.5 Hz), 5.93 (1H, m), 6.79 (1H, s), 7.00 (1H, s), 7.10–7.70 (25H, br s), 8.60 (1H, d, J=9 Hz), 8.73 (1H, br s)

(C) 7.0 g (7.9 mmol) of the compound obtained in the above step (B), was dissolved in 130 ml of dry acetone, and 2.4 g (16 mmol) of sodium iodide was added thereto. The mixture was stirred at 0° C. for 30 minutes. The reaction solution was concentrated under reduced pressure, and the residue was extracted with ethyl acetate. The organic layer was washed with a saturated sodium chloride aqueous solution, then dried over anhydrous sodium sulfate and concentrated under reduced pressure. The residue was purified by silica gel column chromatography (20% ethyl acetate/hexane) to obtain 5.4 g (yield: 70%) of benzhydryl 3-iodomethyl-7-[2-isopropoxyimino-2-(2-tritylaminothiazol-4-yl)acetamido]-3-cephem-4-carboxylate 1-oxide (syn-isomer).

IR(KBr) cm$^{-1}$: 1800, 1730, 1680, 1520

NMR)DMSO-$d_6$) δ: 1.23 (6H, d, J=6 Hz), 3.90 (2H, br s), 4.10–4.60 (3H, m), 5.05 (1H, d, J=4.5 Hz), 5.85 (1H, dd, J=4.5 and 9 Hz), 6.75 (1H, s), 6.97 (1H, s), 7.00–7.60 (25H, m), 8.50 (1H, d, J=9 Hz), 8.70 (1H, br s)

(D) 2.1 g (yield: 84%) of benzhydryl 3-(6,7-dihydroxyisoquinolinio)methyl-7-[2-isopropoxyimino-2-(2-tritylaminothiazol-4-yl)acetamido]-3-cephem-4-carboxylate 1-oxide iodide (syn-isomer) was obtained as a foamy substance from 2.1 g (2.0 mmol) of the compound obtained in the above step (C) and 600 mg (2.3 mmol) of 6,7-dihydroxyisoquinoline hydrobromide monohydrate in the same manner as in Example 1(D).

IR(KBr) cm$^{-1}$: 1800, 1730, 1660, 1630, 1520

NMR(DMSO-$d_6$) δ: 1.20 (6H, d, J=6 Hz), 3.60–4.10 (2H, m), 4.31 (1H, m), 5.13 (1H, m), 5.20–5.70 (2H, m), 5.97 (1H, m), 6.77 (1H, m), 7.00 (1H, m), 7.00–8.20 (29H, m), 8.70 (2H, m), 9.03 (1H, br s)

(E) 2.0 g (yield: 96%) of benzhydryl 3-(6,7-dihydroxyisoquinolinio)methyl-7-[2-isopropoxyimino-2-(2-tritylaminothiazol-4-yl)acetamido]-3-cephem-4-carboxylate iodide (syn-isomer) was obtained from 2.1 g (1.7 mmol) of the compound obtained in the above step (D) in the same manner as in Example 1(E).

NMR(DMSO-$d_6$) δ: 1.20 (6H, d, J=6 Hz), 3.60 (2H, m) 4.20 (1H, m), 5.27 (1H, d, J=4.5 Hz), 5.40–5.80 (2H, m), 5.90 (1H, m), 6.73 (1H, m), 6.92 (1H, m), 7.00–7.80 (26H, m), 8.00–8.60 (4H, m), 9.50–9.70 (2H, m)

(F) 220 mg (yield: 23%) of the above identified compound was obtained from 2.0 g (1.7 mmol) of the compound obtained in the above step (E) in the same manner as in Example 1(F).

Mp: 180° C. (decomposed)

IR(KBr) cm$^{-1}$: 1780, 1670, 1620, 1530

NMR(DMSO-$d_6$) δ: 1.15 (6H, d, J=6 Hz), 3.00–3.70 (2H, m), 4.25 (1H, m), 5.10 (1H, d, J=4.5 Hz), 5.00–5.60 (2H, m), 5.75 (1H, m), 6.65 (1H, s), 7.10 (2H, br s), 7.47 (1H, s), 7.75 (1H, d, J=7 Hz), 8.35 (1H, d, J=7 Hz), 9.30 (1H, s), 9.40 (1H, m)

EXAMPLE 3

Preparation of 7-[2-allyloxyimino-2-(2-aminothiazol-4-yl)acetamido]-3-(6,7-dihydroxyisoquinolinio)methyl-3-cephem-4-carboxylate (syn-isomer)

(A) 2.0 g (yield: 86%) of benzhydryl 7-[2-allyloxyimino-2-(2-tritylaminothiazol-4-yl)acetamido]-3-(6,7-dihydroxyisoquinolinio)methyl-3-cephem-4-carboxylate 1-oxide iodide (syn-isomer) was prepared from 2.0 g (2.0 mmol) of benzhydryl 7-[2-allyloxyimino-2-(2-tritylaminothiazol-4-yl)acetamido]-3-iodomethyl-3-cephem-4-carboxylate 1-oxide (syn-isomer) and 600 mg (2.3 mmol) of 6,7-dihydroxyisoquinoline hydrobromide monohydrate in the same manner as in Example 1(D).

IR(KBr) cm$^{-1}$: 1800, 1730, 1670, 1640, 1530

NMR(DMSO-$d_6$) δ: 3.40–4.10 (2H, m), 4.55 (2H, m), 5.00–5.50 (6H, m), 5.95 (1H, m), 6.95 (1H, s), 7.00 (1H, s), 7.05–8.00 (29H, m), 8.90 (1H, br s)

(B) 2.0 g (yield: 100%) of benzhydryl 7-[2-allyloxyimino-2-(2-tritylaminothiazol-4-yl)acetamido]-3-(6,7-dihydroxyisoquinolinio)methyl-3-cephem-4-carboxylate iodide (syn-isomer) was obtained from 2.0 g (1.8 mmol) of the compound obtained in the above step (A) in the same manner as in Example 1(E).

IR(KBr) cm$^{-1}$: 1790, 1720, 1680, 1640, 1620, 1520

NMR(DMSO-$d_6$) δ: 3.60 (2H, m), 4.55 (2H, m), 5.00–6.00 (7H, m), 6.73 (1H, m), 6.92 (1H, m), 7.00–7.30 (26H, m), 8.00–8.70 (3H, m), 9.60 (1H, m)

(C) 140 mg (yield: 13.5%) of the above identified compound was obtained from 2.0 g (1.8 mmol) of the compound obtained in the above step (B) in the same manner as in Example 1(F).

Mp: 180° C. (decomposed)

IR(KBr) cm$^{-1}$: 1780, 1670, 1620, 1540

NMR(DMSO-$d_6$) δ: 3.00–3.80 (2H, m), 3.52 (2H, m), 5.00–5.60 (6H, m), 5.75 (1H, m), 6.67 (1H, s), 6.90–7,80 (4H, m), 8.30 (1H, m), 9.20 (1H, m), 9.55 (1H, m)

EXAMPLE 4

Preparation of 7-[2-(2-aminothiazol-4-yl)-2-(1-carboxy-1-methylethoxyimino)acetamido]-3-(6,7-dihydroxyisoquinolinio)-methyl-3-cephem-4-carboxylate (syn-isomer)

(A) 28 g (41 mmol) of 2-(1-benzhydryloxycarbonyl-1-methylethoxyimino)-2-(2-tritylaminothiazol-4-yl)acetic acid (syn-isomer) and 17 g (41 mmol) of benzhydryl 7-amino-3-chloromethyl-3-cephem-4-carboxylate, were dissolved in 300 ml of dry methylene chloride, and 15.6 ml (123 mmol) of N,N-dimethylaniline was added thereto. The mixture was cooled to −10° C., and 4 ml (43 mmol) of phosphorus oxychloride was dropwise added thereto. The reaction solution was stirred at room temperature for 2.5 hours, and then concentrated under reduced pressure. The residue was extracted with ethyl acetate. The organic layer was washed sequentially with 1N hydrochloric acid, a 5% sodium hydrogen carbonate aqueous solution and a saturated sodium chloride aqueous solution, then dried over anhydrous sodium sulfate and concentrated under reduced pressure to obtain 36 g (yield: 81%) of benzhydryl 3-chloromethyl-7-[2-(1-benzhydryloxycarbonyl-1-methylethoxyimino)-2-(2-tritylaminothiazol-4-yl)acetamido]-3-cephem-4-carboxylate (syn-isomer).

IR(KBr) cm$^{-1}$: 1790, 1740, 1690, 1530, 1500, 700

NMR(DMSO-$d_6$) δ: 1.45 (6H, br s), 3.62 (2H, m), 4.42 (2H, br s), 5.25 (1H, d, J=4.5 Hz), 5.82 (1H, dd, J=4.5 and 9 Hz), 6.67 (1H, s), 6.77 (1H, s), 6.97 (1H, s), 7.00–7.70 (35H, m), 8.77 (1H, br s), 9.40 (1H, d, J=9 Hz)

(B) 36 g (33 mmol) of the compound obtained in the above step (A), was dissolved in 360 ml of methylene chloride, and 6.0 g (35 mmol) of m-chloroperbenzoic acid was added thereto under cooling with ice. The mixture was stirred at the same temperature for 1 hour. The reaction solution was washed with a 2% sodium metabisulfite aqueous solution, and then concentrated under reduced pressure. The residue was extracted with ethyl acetate. The organic layer was washed with a saturated sodium chloride aqueous solution, then dried over anhydrous sodium sulfate and concentrated under reduced pressure to obtain 36 g (yield: 98%) of benzhydryl 3-chloromethyl-7-[2-(benzhydryloxycarbonyl-1-methylethoxyimino)-2-(2-tritylaminothiazol-4-yl)-acetamido]-3-cephem-4-carboxylate 1-oxide (syn-isomer).

IR(KBr) cm$^{-1}$: 1800, 1730, 1680, 1510, 1490

NMR(DMSO-d$_6$) δ: 1.53 (6H, br s), 3.85 (2H, m), 4.53 (2H, m), 5.10 (1H, d, J=4.5 Hz), 5.97 (1H, m), 6.80 (1H, s), 6.87 (1H, s), 7.00 (1H, s), 7.10–7.70 (35H, m), 8.45 (1H, d, J=9 Hz), 8.77 (1H, br s)

(C) 36 g (33 mmol) of the compound obtained in the above step (B), was dissolved in 500 ml of dry acetone, and 12 g (80 mmol) of sodium iodide was added thereto under cooling with ice. The mixture was stirred at the same temperature for 1 hour. The reaction solution was concentrated under reduced pressure, and the residue was extracted with ethyl acetate. The organic layer was washed sequentially with a 2% sodium metabisulfite aqueous solution and a saturated sodium chloride aqueous solution, then dried over anhydrous sodium sulfate and concentrated under reduced pressure. The residue was purified by silica gel column chromatography (20% ethyl acetate/hexane) to obtain 22.8 g (yield: 58.5%) of benzhydryl 7-[2-(1-benzhydryloxycarbonyl-1-methylethoxyimino-2-tritylaminothiazol-4-yl)acetamido]-3-iodomethyl-3-cephem-4-carboxylate 1-oxide (syn-isomer).

IR(KBr) cm$^{-1}$: 1800, 1730, 1690, 1520, 1500, 700

NMR(DMSO-d$_6$) δ: 1.53 (6H, br s), 3.90 (2H, br 5), 4.43 (2H, m), 5.07 (1H, d, J=4.5 Hz), 5.92 (1H, dd, J=4.5 and 9 Hz), 6.70 (1H, s), 6.78 (1H, s), 7.00 (1H, s), 7.05–7.70 (35H, m), 8.40 (1H, d, J=9 Hz), 8.73 (1H, br s)

(D) 2g (1.7 mmol) of the compound obtained in the above step (C) and 580 mg (2.23 mmol) of 6,7-dihydroxyisoquinoline hydrobromide monohydrate was dissolved in 10 ml of N,N-dimethylformamide, and 0.3 ml (0.21 mmol) of triethylamino was dropwise added thereto at room temperature. The mixture was stirred for 2 hours. The reaction solution was concentrated under reduced pressure, and the residue was extracted with chloroform. The organic layer was washed with a saturated sodium chloride aqueous solution, then dried over anhydrous sodium sulfate and concentrated under reduced pressure. The residue was purified by silica gel column chromatography (5% methanol/chloroform) to obtain 1.65 g (yield: 85.5%) of benzhydryl 7-[2-(1-benzhydryloxycarbonyl-1-methylethoxyimino)-2-(2-tritylaminothiazol-4-yl)acetamido]-3-(6,7-dihydroxyisoquinolinio)methyl-3-cephem-4-carboxylate 1-oxide iodide (syn-isomer).

IR(KBr) cm$^{-1}$: 1800, 1730, 1680, 1630

NMR(DMSO-d$_6$) δ: 1.50 (6H, br s), 3.50–4.10 (2H, m), 5.10 (1H, m), 5.60 (2H, m), 6.00 (1H, m), 6.70 (1H, s), 6.80 (2H, br s), 6.90–8.00 (39H, m), 8.05–8.60 (2H, m), 8.70 (1H, m)

(E) 1.65 g (1.2 mmol) of the compound obtained in the above step (D) and 2 g (12 mmol) of potassium iodide were suspended in dry acetone, and 0.53 ml (0.8 mmol) of acetyl chloride was dropwise added −20° C. The reaction solution was stirred at −10° C. for 5 hours, and then poured into a 2% sodium metabisulfite aqueous solution. The precipitates were collected by filtration and washed with water. The precipitates were dissolved in chloroform, then washed with a saturated sodium chloride aqueous solution, dried over anhydrous sodium sulfate and concentrated under reduced pressure to obtain 1.3 g (yield: 80%) of benzhydryl 7-[2-(1-benzhydryloxycarbonyl-1-methylethoxyimino)-2-(2-tritylaminothiazol-4-yl)acetamido]-3-(6,7-dihydroxyisoquinolinio)methyl-3-cephem-4-carboxylate iodide (syn-isomer).

IR(KBr) cm$^{-1}$: 1790, 1740, 1680, 1640

NMR(DMSO-d$_6$) δ: 1.50 (6H, br s), 3.53 (2H, m), 5.30 (1H, m), 5.50 (2H, m), 5.90 (1H, m), 6.67 (1H, s), 6.75 (2H, br s), 6.90–7.70 (36H, m), 7.90–8.50 (3H, m), 8.80 (1H, m), 9.40 (2H, m)

(F) 1.3 g (0.98 mmol) of the compound obtained in the above step (E), was dissolved in 20 ml of dry methylene chloride, and 1.3 ml of anisole was added thereto. Then, 20 ml of trifluoroacetic acid was dropwise added thereto at 0° C. The reaction solution was stirred at the same temperature for 2.5 hours, and then concentrated under reduced pressure. Ethyl ether was added to the residue, and the precipitates were collected by filtration. The precipitates were dissolved in 200 ml of water, and insoluble substances were removed by filtration. The filtrate was subjected to reversed phase column chromatography (LC-Sorb, manufactured by Chemco Co.), and the fractions containing the desired compound eluted with 5% tetrahydrofuran/water were concentrated and freeze-dried to obtain 120 mg (yield: 20%) of the above identified compound.

Mp: 170° C. (decomposed)

IR(KBr) cm$^{-1}$: 1770, 1620, 1540, 1440, 1290, 1200

NMR(DMSO-d$_6$) δ: 1.40 (6H, br s), 3.00–3.80 (2H, m), 5.15 (1H, d, J=5 Hz), 5.25–5.70 (2H, m), 5.80 (1H, m), 6.70 (1H, s), 7.00–7.50 (3H, m), 7.80 (1H, m), 8.35 (1H, m), 9.35 (2H, m)

EXAMPLE 5

Preparation of 7-[2-(2-aminothiazol-4-yl)-2-(1-carboxy-1-cyclopentyloxyimino)acetamido]-3-(6,7-dihydroxyisoquinolinio)methyl-3-cephem-4-carboxylate (syn-isomer)

(A) 2.12 g (3 mmol) of 2-(1-benzhydryloxycarbonyl-1-cyclopentyloxyimino)-2-(2-tritylaminothiazol-4-yl)acetic acid (syn-isomer) and 1.24 g (3 mmol) of benzhydryl 7-amino-3-chloromethyl-3-cephem-4-carboxylate were dissolved in 50 ml of methylene chloride, and 1.2 ml (9.6 mmol) of N,N-dimethylaniline was added thereto under cooling with ice. Then, 0.29 ml (3.15 mmol) of phosphorus oxychloride was dropwise added thereto and the reaction solution was stirred at the same temperature for 4 hours. To the reaction solution, 30 ml of chloroform and 30 ml of water were added. The organic layer was washed with water and a saturated sodium chloride aqueous solution, then dried over anhydrous sodium sulfate and concentrated to obtain benzhydryl 7-[2-(1-benzhydryloxycarbonyl-1-cyclopentyloxyimino)-2-(2-tritylaminothiazol-4- yl)acetamido]-3-chloromethyl-3-cephem-4-carboxylate (syn-isomer), which was used for the next reaction without purification.

(B) The compound obtained in the above step (A) was dissolved in 50 ml of methylene chloride, and 710 mg (3.3 mmol) of m-chloroperbenzoic acid (purity: 80%) was added under cooling with ice. The mixture was stirred for 20 minutes. To the reaction solution, 30 ml of methylene chloride and 40 ml of a 5% sodium hydrogen carbonate aqueous solution were added. Then, the organic layer was separated, and washed with water and a saturated sodium chloride aqueous solution. The organic layer was dried over anhydrous sodium sulfate and then concentrated to obtain benzhydryl 7-[2-(1-benzhydryloxycarbonyl-1-cyclopentyloxy-imino)-2-(2-tritylaminothiazol-4-yl)acetamido]-3-chloromethyl-4-cephem-4-carboxylate 1-oxide (syn-isomer), which was used for the next reaction without purification.

(C) The compound obtained in the above step (B) was dissolved in 40 ml of acetone, and 990 mg (6.6 mmol) of sodium iodide was added thereto. The mixture was stirred at room temperature for 30 minutes. To the reaction solution, 120 ml of ethyl acetate and 20 ml of a 5% sodium thiosulfate aqueous solution were added and subjected to liquid separation. The organic layer was washed with water and a saturated sodium chloride aqueous solution, then dried over anhydrous sodium sulfate and concentrated. The concentrated residue was subjected to flash silica gel column chromatography (ethyl acetate/n-hexane=½) to obtain the fraction containing the desired product. The fraction was concentrated under reduced pressure, and isopropyl ether was added to the residue, whereby 2.92 g (yield from (A): 80.3%) of powdery benzhydryl 7-[2-(1-benzhydryloxycarbonyl-1-cyclopentyloxyimino)-2-(2-tritylaminothiazol-4-yl)-acetamido]-3-iodomethyl-3-cephem-4-carboxylate 1-oxide (syn-isomer) was obtained.

NMR(DMSO-$d_6$)$\delta$: 1.80(4H, m), 2.10(4H, m), 3.90(2H, m), 4.40(2H, m), 5.10(1H, d, J=5 Hz), 5.95 (1H, dd, J=5 and 9 Hz), 6.77(1H, s), 6.80 (1H, s), 7.35(35H, m), 8.50(1H, d, J=9 Hz), 8.80(1H, br s)

(D) 2.6 g (yield: 92%) of benzhydryl 7-[2-(1-benzhydryloxycarbonyl-1-cyclopentyloxy-imino)-2-(2-tritylaminothiazol-4-yl)acetamido]-3-(6,7-dihydroxyisoquinolinio)methyl-3-cephem-4-carboxylate 1-oxide iodide (syn-isomer) was obtained from 2.5 g (2.1 mmol) of the compound obtained in the above step (C) and 600 mg (2.3 mmol) of 6,7-dihydroxyisoquinoline hydrobromide monohydrate in the same manner as in Example 4(D).

NMR(DMSO-$d_6$)$\delta$: 1.50-2.00(4H, m), 1.70-2.30(4H, m), 3.50-4.10(2H, m), 5.15(1H, m), 5.30-5.70 (2H, m), 6.03(1H, m), 6.73(1H, s), 6.78 (1H, s), 7.00(1H, s), 7.05-8.20(39H, m), 8.40-8.90(2H, m), 9.10(1H, s)

(E) 2.5 g (yield: 97%) of benzhydryl 7-[2-(1-benzhydryloxycarbonyl-1-cyclopentyloxy-imino)-2-(2-tritylaminothiazol-4-yl)acetamido]-3-(6,7-dihydroxyisoquinolinio)methyl-3-cephem-4-carboxylate iodide (syn-isomer) was obtained from 2.6 g (1.9 mmol) of the compound obtained in the above step (D) in the same manner as in Example 4(E).

IR(KBr) cm$^{-1}$: 1790, 1730, 1680, 1640, 1620
NMR(DMSO-$d_6$)$\delta$: 1.40-2.40(8H, m), 3.60(2H, m), 5.30(1H, d, J=4.5 Hz), 5.40-5.80(2H, m), 5.93(1H, dd, J=4.5 and 9 Hz), 6.75(1H, s), 6.78(1H, s), 6.93(1H, s), 7.00-7.80(37H, m), 8.00-8.60(3H, m), 9.20-9.70(2H, m)

(F) 50 mg (yield: 4%) of the above identified compound was obtained from 2.5 g (1.8 mmol) of the compound obtained in the above step (E) in the same manner as in Example 4(F).

Mp: 175° C. (decomposed)
IR(KBr) cm$^{-1}$: 1770, 1670, 1630, 1540
NMR(DMSO-$d_6$)$\delta$: 1.40-2.20(8H, m), 3.20-3.70(2H, m), 5.10(1H, d, J=4.5 Hz), 5.10-5.60(2H, m), 5.78(1H, m), 6.62(1H, s), 6.90-7.50(3H, m), 7.70(1H, m), 8.25 (1H, m), 9.00-9.40(2H, m)

EXAMPLE 6

Preparation of 7-[2-(2-aminothiazol-4-yl)-2-(1-carboxy-1-vinyloxyimino)acetamido]-3-(6,7-dihydroxyisoquinolinio)-methyl-3-cephem-4-carboxylate (syn-isomer)

(A) 6.03 g (20 mmol) of t-butyl 2-phthaloyloxy propenate was dissolved in 200 ml of methylene chloride, and then a mixture of 1.88 ml of 80% hydrazine hydrate and 40 ml of methanol, was dropwise added thereto. The mixture was stirred at room temperature for 1.5 hours, and insoluble substances were removed by filtration. The filtrate was washed 3 times with 8% aqueous ammonia and then with a saturated sodium chloride aqueous solution, and then dried over anhydrous sodium sulfate. The solvent was distilled off under reduced pressure. The residue was dissolved in 120 ml of methanol, and then 7.46 g (18 mmol) of 2-(2-tritylaminothiazol-4-yl)glyoxylic acid was added thereto. The mixture was stirred at room temperature for 3 hours. The precipitated crystals were collected by filtration to obtain 7.08 g (yield: 70.9%) of 2-(1-t-butoxycarbonyl-1-vinyloxyimino)-2-(2-tritylaminothiazol-4-yl)acetic acid (syn-isomer).

IR(KBr) cm$^{-1}$: 3400, 2970, 1725, 1630, 1100, 700
NMR(DMSO-$d_6$)$\delta$: 1.45(9H, s), 5.20(1H, br s), 5.33(1H, br s), 7.05(1H, s), 7.10-7.40(15H, m), 8.82 (1H, br s)

(B) 5.06 g (9.76 mmol) of the compound obtained in the above reaction (A) and 4.05 g (9.76 mmol) of benzhydryl 7-amino-3-chloromethyl-3-cephem-4-carboxylate were dissolved in 100 ml of methylene chloride, and 5.56 ml (43.9 mmol) of N,N-dimethylaniline was added thereto under cooling with ice. Then, 1.07 ml (11.5 mmol) of phosphorus oxychloride was dropwise added thereto. The mixture was stirred at room temperature for 1 hour, then washed sequentially with 0.5N hydrochloric acid and a saturated sodium chloride aqueous solution and dried over anhydrous sodium sulfate. The solvent was distilled off under reduced pressure, and ethyl ether was added to the residue to obtain 8.7 g (yield: 96.7%) of benzhydryl 3-chloromethyl-7-[2-(1-t-butoxycarbonyl-1-vinyloxyimino)-2-(2-tritylaminothiazol-4-yl)acetamido]-3-cephem-4-carboxylate (syn-isomer).

IR(KBr) cm$^{-1}$: 3400, 2960, 1790, 1720, 1520, 1150, 700
NMR(DMSO-$d_6$)$\delta$: 1.48(9H, s), 3.47 and 3.75(2H, ABq, J=18 Hz), 4.45(2H, br s), 5.19(1H, br s), 5.27(1H, d, J=4.5 Hz), 5.35(1H, br s), 5.77(1H, dd, J=4.5 and 7.5 Hz), 6.92(1H, s), 6.95(1H, s), 7.30(25H, m), 8.86(1H, br s), 9.79(1H, d, J=7.5 Hz)

(C) 2.0 g (2.06 mmol) of the compound obtained in the above reaction (B), was dissolved in 30 ml of methylene chloride, and 440 mg (2.55 mmol) of m-chloroperbenzoic acid was added thereto at −10° C. The mixture was stirred at the same temperature for 1 hour. The reaction solution was washed sequentially with a 2% sodium metabisulfite aqueous solution, a 5% sodium hydrogen carbonate aqueous solution and a saturated sodium chloride aqueous solution, then dried over anhydrous sodium sulfate and concentrated under reduced pressure to obtain 2.0 g (yield: 98.4%) of benzhydryl 7-[2-(1-t-butoxycarbonyl-1-vinyloxy)imino-2-(2-tritylaminothiazol-4-yl)acetamido]-3-chloromethyl-3-cephem-4-carboxylate 1-oxide (syn-isomer).

IR(KBr) cm$^{-1}$: 1800, 1730, 1690, 1690, 1640, 1530, 1370

NMR(DMSO-d$_6$)δ: 1.47(9H, s), 3.82(2H, br s), 4.52(2H, m), 5.07(1H, d, J=4.5 Hz), 5.20(1H, br s), 5.35(1H, br s), 5.80(1H, m), 6.97(1H, s), 7.00(1H, s), 7.10-7.60(25H, m), 8.80(1H, br s), 9.37(1H, d, J=10 Hz)

(D) 2.0 g (2.03 mmol) of the compound obtained in the above reaction (C), was dissolved in 40 ml of dry acetone, and 760 mg (5.07 mmol) of sodium iodide was added under cooling with ice. The mixture was stirred at the same temperature for 1 hour. The reaction solution was concentrated under reduced pressure, and the residue was extracted with ethyl acetate. The organic layer was washed sequentially with a 2% sodium metabisulfite aqueous solution and a saturated sodium chloride aqueous solution, then dried over anhydrous sodium sulfate and concentrated under reduced pressure. The residue was subjected to silica gel column chromatography (20% ethyl acetate/hexane) to obtain 1.4 g (yield: 64.0%) of benzhydryl 7-[2-(1-t-butoxycarbonyl-1-vinyloxy)imino-2-(2-tritylaminothiazol-4-yl)acetamido]-3-iodomethyl-3-cephem-4-carboxylate 1-oxide (syn-isomer).

IR(KBr) cm$^{-1}$: 1800, 1720, 1690, 1630, 1530, 1370

NMR(DMSO-d$_6$)δ: 1.47(9H, s), 3.87(2H, m), 4.45(2H, m), 5.07(1H, d, J=4.5 Hz), 5.20(1H, br s), 5.35(1H, br s), 5.80(1H, m), 6.98(1H, s), 7.01(1H, s), 7.10-7.60(25H, m), 8.83(1H, br s), 9.35(1H, d, J=9 Hz)

(E) 1.4 g (1.3 mmol) of the compound obtained in the above reaction (D) and 380 mg (1.46 mmol) of 6,7-dihydroxyisoquinoline hydrobromide monohydrate were dissolved in 7 ml of N,N-dimethylformamide, and 0.19 ml (1.37 mmol) of triethylamine was dropwise added thereto. The reaction solution was stirred at room temperature for 2 hours, and then concentrated under reduced pressure. The residue was extracted with chloroform. The organic layers was washed sequentially with water and a saturated sodium chloride aqueous solution, then dried over anhydrous sodium sulfate and concentrated under reduced pressure to obtain 1.2 g (yield: 74.6%) of benzhydryl 7-[2-(1-t-butoxycarbonyl-1-vinyloxy)imino-2-(2-tritylaminothiazol-4-yl)acetamido]-3-(6,7-dihydroxyisoquinolinio)methyl-3-cephem-4-carboxylate 1-oxide iodide (syn-isomer).

IR(KBr) cm$^{-1}$: 1800, 1720, 1670, 1640, 1530, 1450

NMR(DMSO-d$_6$)δ: 1.50(9H, s), 3.50-3.75(2H, m), 5.10(1H, d, J=4.5 Hz), 5.10-5.40(4H, m), 5.87(1H, m), 7.00(2H, s), 7.05-8.20(28H, m), 8.60-9.00(2H, m), 9.40(1H, m)

(F) 1.2 g (0.97 mmol) of the compound obtained in the above reaction (E) and 1.6 g (9.6 mmol) of potassium iodide were suspended in 30 ml of dry acetone, and 0.35 ml (4.9 mmol) of acetyl chloride was dropwise added thereto at −20° C. The reaction solution was stirred at −10° C. for 4 hours, and poured into 150 ml of a 2% sodium metabisulfite aqueous solution. The precipitates were collected by filtration and washed with water. The precipitates were dissolved in chloroform and washed with a saturated sodium chloride aqueous solution. The organic layer was dried over anhydrous sodium sulfate and then concentrated under reduced pressure to obtain 1.1 g (yield: 92.9%) of benzhydryl 7-[2-(1-t-butoxycarbonyl-1-vinyloxy)imino-2-(2-tritylaminothiazol-4-yl)acetamido]-3-(6,7-dihydroxyisoquinolinio)methyl-3-cephem-4-carboxylate iodide (syn-isomer).

IR(KBr) cm$^{-1}$: 1790, 1720, 1690, 1640, 1530, 1370

NMR(DMSO-d$_6$)δ: 1.52(9H, s), 3.40-3.70(2H, m), 5.10-6.95 (6H, m), 6.90(1H, s), 6.92(1H, s), 7.00-7.70(27H, m), 7.90-8.60(2H, m), 8.75(1H, m), 9.35(1H, m), 9.73(1H, m)

(G) 1.1 g (0.9 mmol) of the compound obtained in the above reaction (F), was dissolved in 7 ml of dry methylene chloride, and 1.1 ml of anisole was added. Then, 15 ml of trifluoroacetic acid was dropwise added at 0° C. The reaction solution was stirred at the same temperature for 2.5 hours, and then concentrated under reduced pressure. Ethyl ether was added to the residue, and the precipitates were collected by filtration. The precipitates were dissolved in 50 ml of a 10% methanol aqueous solution, and insoluble substances were removed by filtration. The filtrate was subjected to reversed phase column chromatography (LC-Sorb, manufactured by Chemco Co.), and the fractions containing the desired compounds eluted with 20% methanol/water were concentrated and freeze-dried to obtain 40 mg (yield: 7.3%) of the above identified compound.

Mp: 155° C. (decomposed)

IR(KBr) cm$^{-1}$: 1770, 1630, 1530, 1440

NMR(DMSO-d$_6$)δ: 3.10-3.80(2H, m), 5.00-5.65(5H, m), 5.80 (1H, m), 6.95(1H, s), 7.30(1H, m), 7.95 (2H, m), 8.45(1H, m), 9.25(1H, m), 9.75(1H, m)

EXAMPLE 7

Preparation of 7-[2-(2-aminothiazol-4-yl)-2-(2-propynyloxyimino)acetamido]-3-(6,7-dihydroxy-isoquinoliniomethyl)-3-cephem-4-carboxylate (syn-isomer)

(A) The same operation as in Example 1(A), (B) and (C) was conducted by using 3.0 g (6.9 mmol) of 2-(2-propynyloxyimino)-2-(2-tritylaminothiazol-4-yl)-acetic acid (syn-isomer) and 2.86 g (6.9 mmol) of benzhydryl 7-amino-3-chloromethyl-3-cephem-4-carboxylate, whereby 3.8 g (yield: 58.7%) of benzhydryl 3-iodomethyl-7-[2-(2-propynyloxyimino)-2-(2-tritylaminothiazol-4-yl)-acetamido]-3-cephem-4-carboxylate 1-oxide (syn-isomer) was obtained.

IR(KBr) cm$^{-1}$: 2120, 1800, 1730, 1690, 1520

NMR(DMSO-d$_6$)δ: 3.45(2H, s), 3.90(2H, br s), 4.40(2H, m), 4.70(2H, s), 5.05(1H, d, J=4.5 Hz), 5.85 (1H, dd, J=4.5 and 8 Hz), 6.85(1H, s), 6.98(1H, s), 7.10-7.70(25H, m), 8.80(1H, s), 9.00(1H, d, J=8 Hz)

(B) The same operation as in Example 1(D), (E) and (F) was conducted by using 2.0 g (2.1 mmol) of the compound obtained in the above reaction (A) and 600 mg (2.3 mmol) of 6,7-dihydroxyisoquinoline hydrobromide monohydrate, whereby 180 mg (yield: 12.6%) of the above identified compouned was obtained.

Mp: 160° C. (decomposed)

IR(KBr) cm$^{-1}$: 2120, 1770, 1670, 1610, 1540

NMR(DMSO-d$_6$)δ: 3.00-3.70(3H, m), 4.65(2H, br s), 5.13(1H, d, J=4.5 Hz), 5.25-6.00(3H, m), 6.73(1H, s), 7.18(2H, br s), 7.50(1H, s), 7.80(1H, d, J=6 Hz), 8.40(1H, d, J=6 Hz), 9.33(1H, br s), 9.60(1H, m)

EXAMPLE 8

Preparation of
3-(6,7-diacetoxyisoquinoliniomethyl)-7-[2-(2-aminothiazol-4-yl)-2-methoxyiminoacetamido]-3-cephem-4-carboxylate (syn-isomer)

The same operation as in Example 1(D), (E) and (F) was conducted by using 2.5 g (2.7 mmol) of benzhydryl 3-iodemethyl-7-[2-methoxyimino-2-(2-tritylaminothiazol-4-yl)acetamido]-3-cephem-4-carboxylate 1-oxide (syn-isomer) obtained in Example 1(C) and 1.0 g (4.0 mmol) of 6.7-diacetoxyisoquinoline, whereby 25 mg (yield: 1.4%) of the above identified compound was obtained.

Mp: 185° C. (decomposed)
IR(KBr) cm$^{-1}$: 1780, 1620, 1540, 1380, 1200
NMR(DMSO-d$_6$)δ: 2.30(3H, s), 2.50(3H, s), 3.20–3.70(2H, m), 3.80(3H, s), 4.80–5.60(3H, m), 5.73 (1H, m), 6.70(1H, s), 7.00(1H, br s), 7.15(1H, m), 7.75(2H, m), 8.27(1H, m), 9.17(1H, m), 9.53(1H, m)

EXAMPLE 9

Preparation of sodium
3-(6,7-diacetoxyisoquinolino)methyl-7-[2-(1-carboxylate-1-methylethoxyimino)-2-(2-aminothiazol-4-yl)acetamide]-3-cephem-4-carboxylate (syn-isomer)

The same operation as in Example 1(D), (E) and (F) was conducted by using 2.5 g of the compound obtained in Example 4(C) and 728 mg (3.16 mmol) of 6,7-diacetoxyisoquinoline, and then the amino-protecting group and carboxyl-protecting group were removed, whereby the trifluoroacetic acid salt of the desired compound was obtained. The salt was suspended in water, and adjusted to pH 7.0 with a saturated sodium hydrogen carbonate aqueous solution. Then, insoluble substances were removed by filtration. The filtrate was subjected to reversed phase column chromatography (LC-Sorb, manufactured by Chemco Co.), and the fractions 5% methanol/water were concentrated and freeze-dried to obtain 123 mg (yield: 7%) of the above identified compound.

MP: 175° C. (decomposed)
IR(KBr) cm$^{-1}$: 3400, 1765, 1595
NMR(DMSO-d$_6$)δ: 1.40(3H, br s), 1.46(3H, br s), 2.30(6H, s), 4.30–5.30(3H, m), 6.00(1H, m), 6.85(1H, s), 7.00–9.10(5H, m)

REFERENCE EXAMPLE 1

Preparation of
7-[2-(2-aminothiazol-4-yl)-2-(1-carboxylate-1-methylethoxyimino)acetamido]-3-isoquinoliniomethyl-3-cephem-4-carboxylate monosodium salt (syn-isomer)

450 mg (0.48 mmol) of 3-acetoxymethyl-7-[2-(1-benzhydryloxycarbonyl-1-methylethoxyimino)-2-(2-tritylaminothiazol-4-yl)acetamido]-3-cephem-4-carboxylic acid and 15 mg (0.085 mmol) of ascorbic acid were dissolved in 3 ml of acetone, and 1 ml of water, 2.88 g (19.2 mmol) of sodium iodide and 0.6 ml (50 mmol) of isoquinoline were added thereto. The mixture was stirred at from 50° to 60° C. for 5 hours. The reaction solution was extracted with chloroform, then dried over anhydrous sodium sulfate and concentrated under reduced pressure. The residue was dissolved in 5 ml of dry methylene chloride, and 0.5 ml of anisole was added. Then, 5 ml of trifluoroacetic acid was dropwise added thereto at 0° C. The mixture was stirred at the same temperature for 2 hours. The reaction solution was concentrated under reduced pressure, and ethyl ether was added to the residue. The precipitates were collected by filtration. Then, precipitates were dissolved in 100 ml of water and adjusted to pH 6.5 with a sodium hydrogen carbonate aqueous solution. Then, insoluble substances were removed by filtration. The filtrate was subjected to reversed phase column chromatography (LC-Sorb, manufactured by Chemco Co.), and the fractions containing the desired compound eluted with 5% methanol/water were concentrated and freeze-dried to obtain 15 mg (yield: 5%) of the above identified compound.

NMR(DMSO-d$_6$)δ: 1.38(6H, br s), 3.10–3.70(2H, m), 5.05 (1H, d, J=5 Hz), 5.70(1H, m), 6.65(1H, s), 7.10(2H, m), 7.90–8.60(6H, m), 9.25(1H, m)

REFERENCE EXAMPLE 2

Preparation of
7-[2-(2-aminothiazole-4-yl)-2-methoxyiminoacetamido]-3-(5-hydroxyisoquinolino)-methyl-3-cephem-4-carboxylate (syn-isomer)

500 mg (0.99 mmol) of cefotaxime formic acid salt was dissolved in a solution of 15 ml of 50% aqueous aceton, and 5.95 g (39.7 mmol) of sodium iodide, 1.43 g (9.9 mmol) of 5-hydroxyisoquinoline and 30 mg of ascorbic acid were added thereto. The mixture was stirred at 60°–65° C. for 4 hours. The reaction mixture was cooled, and 40 ml of aceton was added thereto. The mixture was subjected to silica gel column chromatography (Wakogel C-300) eluting with 10% aceton/water. The fractions containing the desired compound were combined and concentrated to about 40 ml under reduced pressure. The concentrate was charged on reversed phase column chromatography (LC-Sorb, manufactured by Chemco Co.), which was eluated with 20% methanol/water. The fractions containing the desired compound were combined, concentrated and freeze-dried to obtain 72 mg (yield: 13.4%) of the above identified compound.

MP: 195° C. (decomposed)
IR(KBr) cm$^{-1}$: 1770, 1610, 1530, 1400, 1290
NMR(DMSO-d$_6$) δ: 3.00–3.60 (2H, m), 3.80 (3H, s), 5.10 (1H, d, J=4.5 Hz), 5.20–5.90 (3H, m), 6.72 (1H, s), 7.55 (1H, m), 7.87 (2H, m), 8.50 (1H, d, J=6.0 Hz), 8.95 (1H, d, J-6.0 Hz), 10.18 (1H, s)

REFERENCE EXAMPLE 3

Preparation of
7-[2-(2-aminothiazol-4-yl)-2-methoxyiminoacetamido]-3-(8-hydroxyisoquinolino)-methyl-3-cephem-4-carboxylate (syn-isomer)

The same operation as in Reference Example 2 was conducted by using 500 mg (0.99 mmol) of cefotaxime formic acid salt and 1.43 g (9.9 mmol) of 8-hydroxyisoquinoline whereby 52 mg (yield: 9.7%) of the above identified compound was obtained.

MP: 185° C. (decomposed)
IR(KBr) cm$^{-1}$: 1770, 1600, 1530, 1380, 1300
NMR(DMSO-d$_6$) δ: 3.20–3.60 (2H, m), 3.80 (3H, s), 5.10 (1H, d, J=4.5 Hz), 5.20–5.90 (3H, m), 6.63 (1H, s), 7.30 (1H, d, J=7.0 Hz), 7.60 (1H, d, J=7.0 Hz), 8.03 (1H, d, J=7.0 Hz), 8.30 (1H, d, J=6.0 Hz), 8.80 (1H, d, J=6.0 Hz), 10.23 (1H, s)

REFERENCE EXAMPLE 4

Preparation of sodium 7-[2-(2-aminothiazol-4-yl)-2-(1-carboxylate-1-methylethoxyimino)acetamido]-3-(5-hydroxyisoquinolino)-methyl-3-cephem-4-carboxylate (syn-isomer)

The same operation as in Reference Example 1 was conducted by using 1.0 g (1.07 mmol) of 3-acetoxymethyl-7-[2-(1-benzhydryloxycarbonyl-1-methylethoxyimino)-2-(2-tritylaminothiazol-4-yl)acetamido]-3-cephem-4-carboxylic acid (syn-isomer) and 1.55 g (10.7 mmol) of 5-hydroxyisoquinoline, whereby 46 mg (yield: 6.8%) of the above identified compound was obtained.

MP: 205° C. (decomposed)

IR(KBr) cm$^{-1}$: 1770, 1600, 1530, 1400, 1290

NMR(DMSO-d$_6$) δ: 1.40 (6H, br s), 3.20–3.60 (2H, m), 5.07 (1H, d, J=4.5 Hz), 5.20–5.90 (3H, m), 6.70 (1H, s), 7.55 (1H, m), 7.65 (2H, m), 8.45 (1H, m), 8.70 (1H, m), 10.00 (1H, s)

REFERENCE EXAMPLE 5

Preparation of 6,7-dihydroxyisoquinoline hydrobromide monohydrate (A) 73 g (0.23 mol) of 3,4-bis(benzyloxy)benzaldehyde was dissolved in 500 ml of benzene, and 25 ml (0.23 mol) of aminoacetaldehyde diethylacetal was added thereto. The mixture was stirred under reflux for 5 hours to remove the resulting water. The reaction solution was concentrated under reduced pressure to obtain a residue of 2-{N-[3,4-bis(benzyloxy)benzyliden-]amino}acetaldehyde diethylacetal. This residue was dissolved in 700 ml of methanol, and 6.0 g (0.16 mol) of sodium borohydride was added thereto at room temperature. The mixture was stirred for 15 minutes. The reaction solution was concentrated under reduced pressure. The residue was dissolved in ethyl acetate, then washed with a saturated a sodium chloride aqueous solution, dried over anhydrous sodium sulfate and concentrated under reduced pressure to obtain a residue of 2-{N-[3,4-bis(benzyloxy)benzyl]-amino}acetaldehyde diethylacetal. This residue was dissolved in 600 ml of dry tetrahydrofuran, and 39.8 g (0.21 mol) of p-toluenesulfonyl chloride and 59 ml (0.42 mol) of triethylamine were added. The mixture was stirred at room temperature for 17.5 hours. The reaction solution was concentrated under reduced pressure, and the residue was extracted with ethyl acetate. The organic layer was washed with a saturated sodium chloride aqueous solution, then dried over anhydrous sodium sulfate and concentrated under reduced pressure. The residue was subjected to silica gel column chromatography (10% ethyl acetate/hexane), whereby 70 g (yield: 54.3%) of 2-{N-(P)-trisulfonyl-N[3,4-bis(benzyloxy)benzyl]amino}-acetaldehyde diethyl acetal was obtained.

Mp: 75° C.

IR(KBr) cm$^{-1}$: 1600, 1520, 1460, 1340, 1250, 1160, 1130

NMR(DMSO-d$_6$) δ: 1.00 (6H, t, J=7.5 Hz), 2.35 (3H, s), 3.07 (2H, d, J=6 Hz), 3.20–3.60 (6H, m), 4.32 (2H, s), 4.35 (1H, d, J=6 Hz), 4.90 (2H, s), 5.08 (2H, s), 6.60–7.80 (22H, m)

(B) 22.1 g (39 mmol) of the compound obtained in the above step (A), was dissolved in 300 ml of dioxane, and 28 ml of 6N hydrochloric acid was added thereto. Then, the mixture was stirred under reflux for 5.5 hours in a nitrogen atmosphere at a dark place. The reaction solution was adjusted to pH 10.0 with a 20% sodium hydroxide aqueous solution, and then concentrated under reduced pressure. Then, the residue was extracted with ethyl acetate. The organic layer was washed with a saturated sodium chloride aqueous solution, then dried over anhydrous sodium sulfate and concentrated under reduced pressure. The residue was purified by silica gel column chromatography (2% methanol/chloroform) to obtain 8.6 g (yield: 64%) of 6,7-bis(benzyloxy)isoquinoline.

Mp: 97° C.

IR(KBr) cm$^{-1}$: 1620, 1580, 1500, 1240, 1140, 1000

NMR(DMSO-d$_6$) δ: 5.30 (4H, s), 7.25–7.80 (13H, m), 8.30 (1H, d, J=6 Hz), 9.02 (1H, s)

(C) 7.8 g (23 mmol) of the compound obtained in the above step (B) was dissolved in a mixture of 150 ml of methanol and 1.7 ml of 40% hydrobromic acid, and the mixture was stirred at from 50° to 60° C. for 7.5 hours under a hydrogen atmosphere. The reaction solution was filtered, and the filtrate was concentrated under reduced pressure. The residue was recrystallized from a 1N hydrobromic acid aqueous solution to obtain 4.75 g (yield: 79.4%) of the above identified compound.

Mp: 205° C.

IR(KBr) cm$^{-1}$: 1630, 1610, 1520, 1480, 1430, 1300

NMR(DMSO-d$_6$) δ: 7.50 (1H, s), 7.70 (1H, s), 8.10 (1H, ABq, J=6 Hz), 8.30 (1H, ABq, J=6 Hz), 9.42 (1H, s)

Elemental analysis: as $C_9H_7NO_2.H_2O.HBr$. Calculated (%): C 41.56, H 3.88, N 5.39, Br 30.72. Found (%): C 41.51, H 3.85, N 5.24, Br 30.10.

REFERENCE EXAMPLE 6

Preparation of 6,7-dihydroxyisoquinoline hydrobromide monohydrate 1.9 g (10 mmol) of 6,7-dimethoxyisoquinoline was dissolved in a mixture of 15 ml of acetic acid and 15 ml of 40% hydrobromic acid, and the solution was stirred under reflux for 24 hours under a nitrogen atmosphere. The reaction solution was concentrated under reduced pressure. The residue was recrystallized from a 1N hydrobromic acid aqueous solution to obtain 2.3 g (yield: 88.4%) of the above identified compound. The melting point, infrared spectrum and NMR spectrum agreed to those of the compound of Reference Example 5.

REFERENCE EXAMPLE 7

Preparation of 6,7-diacetoxyisoquinoline 500 mg (1.9 mmol) of 6,7-dihydroxyisoquinoline hydrobromide monohydrate was suspended in 10 ml of trifluoroacetic acid, and 2.0 ml (21 mmol) of acetic anhydride was added thereto at room temperature. The mixture was stirred at the same temperature for 24 hours. The reaction solution was concentrated under reduced pressure. Water and ethyl acetate were added to the residue. Then, the aqueous solution was adjusted to pH 8.0 with a 5% sodium hydrogen carbonate aqueous solution, and extracted with ethyl acetate. The extract was washed with a saturated sodium chloride aqueous solution, then dried over anhydrous sodium sulfate and concentrated under reduced pressure to obtain 440 mg (yield: 93.4%) of the above identified compound.

IR(KBr) cm$^{-1}$: 1770, 1620, 1500, 1460, 1380, 1200

NMR(DMSO-d$_6$) δ: 2.39 (6H, s), 7.85 (1H, d, J=6 Hz), 7.90 (1H, s), 8.05 (1H, s), 8.53 (1H, d, J=6 Hz), 9.30 (1H, s)

The compounds of the present invention are novel compounds not disclosed in literatures. They exhibit excellent antibacterial activities particularly against sensitive and resistant Gram-positive and Gram-negative bacteria. They have strong antibacterial activities particularly against resistant Gram-negative bacteria including Pseudomonas aeruginosa, excellent stability against β-lactamase and low β-lactamase-inducing activity, and thus they are effected as antibacterial agents.

In particular, the compounds of the present invention having a 6,7-dihydroxyisoquinoliniomethyl group, wherein hydroxyl groups are introduced at the 6- and 7-positions of the isoquinoline nucleus of the isoquinoliniomethyl group at the 3-position, particularly the compounds of Examples 1 to 6, exhibit unexpectedly strong antibacterial activities against sensitive and resistant Gram-negative bacteria as compared with the compound wherein the isoquinoline nucleus has no substituent (the compound of Reference Example 1).

What is claimed is:

1. A compound having the formula:

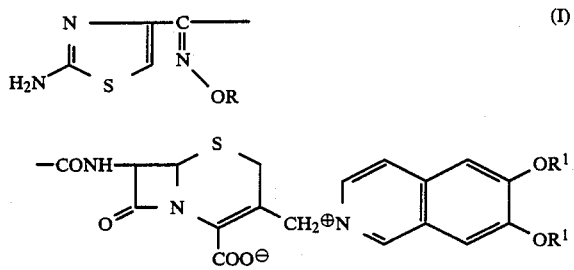

wherein R is a straight chain, branched chain or cyclic lower alkyl, lower alkenyl or lower alkynyl group which may be substituted by a carboxyl group, and $R^1$ is a hydrogen atom or an acetyl group; or a pharmaceutically acceptable salt, physiologically hydrolyzable ester or solvate thereof.

2. The compound according to claim 1, wherein R is methyl, ethyl, n-propyl, isopropyl, n-butyl, carboxymethyl, 1-carboxy-1-methylethyl, cyclopropyl, cyclobutyl, cyclopentyl, cyclohexyl, 1-carboxy-1-cyclopropyl, 1-carboxy-1-cyclobutyl, 1-carboxy-1-cyclopentyl, 1-carboxy-1-cyclohexyl, vinyl, allyl, isopropenyl, 1,1-dimethylallyl, 2-butenyl, 1-carboxyvinyl, 1-carboxyallyl, 2-carboxyallyl, 1-carboxymethylvinyl, ethynyl, 2-propynyl, 2-carboxyethynyl, 1-carboxy-2-propynyl or 3-carboxy-2-propynyl.

3. The compound according to claim 1, wherein $R^1$ is a hydrogen atom.

4. The compound according to claim 1, wherein $R^1$ is an acetyl group.

5. The compound according to claim 1, wherein R is a lower alkyl group which may be substituted by a carboxyl group.

6. The compound according to claim 1, which is 7-[(Z)-2-(2-aminothiazol-4-yl)-2-methoxyiminoacetamido]-3-(6,7-dihydroxyisoquinolinio)methyl-3-cephem-4-carboxylate, 7-[(Z)-2-(2-aminothiazol-4-yl)-2-ethoxyiminoacetamido]-3-(6,7-dihydroxyisoquinolinio)methyl-3-cephem-4-carboxylate, 7-[(Z)-2-(2-aminothiazol-4-yl)-2-isopropoxyiminoacetamido]-3-(6,7-dihydroxyisoquinolinio)methyl-3-cephem-4-carboxylate, 7-[(Z)-2-(2-aminothiazol-4-yl)-2-n-propoxyiminoacetamido]-3-(6,7-dihydroxyisoquinolinio)methyl-3-cephem-4-carboxylate, 7-[(Z)-2-(2-aminothiazol-4-yl)-2-allyloxyiminoacetamido]-3-(6,7-dihydroxyisoquinolinio)methyl-3-cephem-4-carboxylate, 7-[(Z)-2-(2-aminothiazol-4-yl)-2-(2-propynyloxyimino)-acetamido]-3-(6,7-dihydroxyisoquinolinio)methyl-3-cephem-4-carboxylate, 7-[(Z)-2-(2-aminothiazol-4-yl)-2-carboxymethoxyiminoacetamido]-3-(6,7-dihydroxyisoquinolinio)methyl-3-cephem-4-carboxylate, 7-[(Z)-2-(2-aminothiazol-4-yl)-2-(1-carboxy-1-methylethoxyimino)acetamido]-3-(6,7-dihydroxyisoquinolinio)-methyl-3-cephem-4-carboxylate, 7-[(Z)-2-(2-aminothiazol-4-yl)-2-(1-carboxy-1-vinyloxyimino)acetamido]-3-(6,7-dihydroxyisoquinolinio)methyl-3-cephem-4-carboxylate, 7-[(Z)-2-(2-aminothiazol-4-yl)-2-(1-carboxy-1-cyclopropoxyimino)acetamido]-3-(6,7-dihydroxyisoquinolinio)-methyl-3-cephem-4-carboxylate, 7-[(Z)-2-(2-aminothiazol-4-yl)-2-(1-carboxy-1-cyclobutoxyimino)acetamido]-3-(6,7-dihydroxyisoquinolinio)-methyl-3-cephem-4-carboxylate, 7-[(Z)-2-(2-aminothiazol-4-yl)-2-(1-carboxy-1-cyclopentyloxyimino)acetamido]-3-(6,7-dihydroxyisoquinolinio)-methyl-3-cephem-4-carboxylate, 3-(6,7-diacetoxyisoquinolinio)methyl-7-[(Z)-2-(2-aminothiazol-4-yl)-2-methoxyiminoacetamido]-3-cephem-4-carboxylate or 3-(6,7-diacetoxyisoquinolinio)methyl-7-[(Z)-2-(2-aminothiazol-4-yl)-2-(1-carboxy-1-methylethoxyimino)-acetamido]-3-cephem-4-carboxylate.

7. An antibacterial agent comprising an antibacterially effective amount of a compound having the formula:

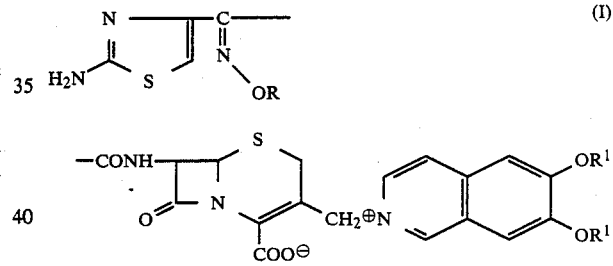

wherein R is a straight chain, branched chain or cyclic lower alkyl, lower alkenyl or lower alkynyl group which may be substituted by a carboxyl group, and $R^1$ is a hydrogen atom or an acetyl group; or a pharmaceutically acceptable salt, physiologically hydrolyzable ester or solvate thereof, and a pharmaceutically acceptable carrier.

8. The antibacterial agent according to claim 7 which is effective against glucose non-fermentative Gram-negative rods.

9. The antibacterial agent according to claim 7 which is effective against pseudomonads.

10. A method for treating disease caused by the infection of bacteria which comprises administering to a subject in need of treatment an antibacterially effective amount of the compound according to claim 1.

11. The method according to claim 10 wherein the compound is used against glucose non-fermentative Gram-negative rods.

12. The method according to claim 10 wherein the compound is used against pseudomonads.

* * * * *